(12) United States Patent
Dennis et al.

(10) Patent No.: US 7,627,376 B2
(45) Date of Patent: Dec. 1, 2009

(54) INTRAVASCULAR MEDICAL DEVICE

(75) Inventors: Charles L. Dennis, Lake Elmo, MN (US); George J. Klein, London (CA); Ursula Gebhardt, Sint Lambrechts Woluwe (BE); Kenneth M. Anderson, Bloomington, MN (US); Glenn C. Zillmer, Hudson, WI (US)

(73) Assignee: Medtronic, Inc., Minneapolis, MN (US)

( * ) Notice: Subject to any disclaimer, the term of this patent is extended or adjusted under 35 U.S.C. 154(b) by 462 days.

(21) Appl. No.: 11/342,735

(22) Filed: Jan. 30, 2006

(65) Prior Publication Data

US 2007/0179552 A1 Aug. 2, 2007

(51) Int. Cl.
*A61N 1/372* (2006.01)
*A61N 1/38* (2006.01)
*A61N 1/39* (2006.01)

(52) U.S. Cl. ............................................. 607/36; 607/4
(58) Field of Classification Search ............. 607/33–37, 607/61
See application file for complete search history.

(56) References Cited

U.S. PATENT DOCUMENTS

| | | | |
|---|---|---|---|
| 3,563,245 A * | 2/1971 | McLean et al. ............. 607/35 |
| 3,906,960 A | 9/1975 | Lehr |
| 3,943,936 A | 3/1976 | Rasor et al. |
| 4,399,820 A | 8/1983 | Wirtzfeld et al. |
| 4,453,537 A | 6/1984 | Spitzer |
| 4,661,107 A | 4/1987 | Fink |
| 4,815,469 A | 3/1989 | Cohen et al. |
| 4,967,755 A | 11/1990 | Pohndorf |
| 5,107,856 A | 4/1992 | Kristiansen et al. |
| 5,170,802 A | 12/1992 | Mehra |
| 5,193,540 A | 3/1993 | Schulman et al. |
| 5,273,053 A | 12/1993 | Pohndorf |
| 5,314,451 A | 5/1994 | Mulier |
| 5,431,694 A * | 7/1995 | Snaper et al. ............. 607/35 |
| 5,814,089 A | 9/1998 | Stokes |
| 5,843,132 A | 12/1998 | Ilvento |
| 6,216,038 B1 | 4/2001 | Hartlaub et al. |
| 6,242,827 B1 | 6/2001 | Wolf et al. |
| 6,409,674 B1 | 6/2002 | Brockway et al. |
| 6,419,692 B1 | 7/2002 | Yang et al. |

(Continued)

FOREIGN PATENT DOCUMENTS

EP 453761 A1 3/1991

(Continued)

OTHER PUBLICATIONS

Nonfinal Office Action dated May 20, 2008 from U.S. Appl. No. 11/342,734 (10 pages).

(Continued)

*Primary Examiner*—Carl H Layno
*Assistant Examiner*—Jessica Reidel
(74) *Attorney, Agent, or Firm*—Stephen W. Bauer

(57) ABSTRACT

An implantable medical device is configured so that all of the major components including a housing and attached leads are disposed within the vasculature of a patient. A tether extends from the housing of the device to an implant location where the tether is secured to tissue outside of the vasculature. In this manner, an intravascular medical device may be implanted at a location remote from final placement, delivered via the vasculature and anchored at the initial entry point.

29 Claims, 27 Drawing Sheets

U.S. PATENT DOCUMENTS

| | | | |
|---|---|---|---|
| 6,425,895 B1 | 7/2002 | Swanson et al. | |
| 6,442,413 B1 | 8/2002 | Silver | |
| 6,477,420 B1 | 11/2002 | Struble et al. | |
| 6,768,246 B2 | 7/2004 | Pelrine et al. | |
| 6,907,285 B2 | 6/2005 | Denker et al. | |
| 6,941,169 B2 | 9/2005 | Pappu | |
| 7,011,671 B2 | 3/2006 | Welch | |
| 7,072,171 B1 | 7/2006 | Muffoletto et al. | |
| 7,309,354 B2 | 12/2007 | Mathis et al. | |
| 2002/0026228 A1 | 2/2002 | Schauerte | |
| 2002/0090389 A1 | 7/2002 | Humes et al. | |
| 2002/0133224 A1 | 9/2002 | Bajgar et al. | |
| 2002/0183823 A1 | 12/2002 | Pappu | |
| 2003/0032892 A1 | 2/2003 | Erlach et al. | |
| 2003/0114905 A1 | 6/2003 | Kuzma | |
| 2003/0158584 A1 | 8/2003 | Cates et al. | |
| 2004/0021322 A1* | 2/2004 | Ariav | 290/1 R |
| 2004/0073267 A1 | 4/2004 | Holzer | |
| 2004/0147973 A1* | 7/2004 | Hauser | 607/36 |
| 2004/0158294 A1 | 8/2004 | Thompson | |
| 2004/0215049 A1 | 10/2004 | Zdeblick et al. | |
| 2004/0220637 A1 | 11/2004 | Zdeblick et al. | |
| 2004/0249417 A1 | 12/2004 | Ransbury et al. | |
| 2004/0249431 A1* | 12/2004 | Ransbury et al. | 607/126 |
| 2005/0043765 A1 | 2/2005 | Williams et al. | |
| 2005/0080472 A1* | 4/2005 | Atkinson et al. | 607/126 |
| 2005/0085870 A1 | 4/2005 | Goroszeniuk | |
| 2005/0137672 A1* | 6/2005 | Coe et al. | 607/126 |
| 2005/0154437 A1* | 7/2005 | Williams | 607/123 |
| 2005/0187584 A1 | 8/2005 | Denker et al. | |
| 2005/0288717 A1 | 12/2005 | Sunagawa | |
| 2006/0135999 A1* | 6/2006 | Bodner et al. | 607/4 |
| 2007/0123861 A1 | 5/2007 | Dewey et al. | |
| 2007/0179550 A1* | 8/2007 | Dennis et al. | 607/36 |
| 2007/0179552 A1 | 8/2007 | Dennis et al. | |
| 2007/0179581 A1* | 8/2007 | Dennis et al. | 607/119 |

FOREIGN PATENT DOCUMENTS

| | | |
|---|---|---|
| WO | WO9211898 A1 | 7/1992 |
| WO | WO2004110263 | 12/2004 |
| WO | WO2004110263 A1 | 12/2004 |
| WO | WO2005000398 A2 | 1/2005 |
| WO | WO2005058415 A2 | 6/2005 |
| WO | WO2005077450 A2 | 8/2005 |
| WO | WO2006065394 A1 | 6/2006 |
| WO | WO2007053508 A1 | 5/2007 |
| WO | WO2007059386 A2 | 5/2007 |
| WO | WO2007090013 A2 | 8/2007 |
| WO | WO2007090023 A1 | 8/2007 |

OTHER PUBLICATIONS

Amendment and Response filed Oct. 17, 2008 for U.S. Appl. No. 11/342,734 (10 pages).

Notice of Allowance dated Jan. 28, 2009 from U.S. Appl. No. 11/342,734 (9 pages).

Nonfinal Office Action dated Jan. 26, 2009 from U.S. Appl. No. 11/342,948 (10 pages).

International Search Report from PCT Application Serial No. PCT/US2007/061021 dated May 24, 2007 (4 pages).

Written Opinion from PCT Application Serial No. PCT/US2007/061021 dated Jul. 30, 2008 (8 pages).

International Search Report from PCT Application Serial No. PCT/US2006/060556 dated Nov. 14, 2007 (5 pages).

Written Opinion from PCT Application Serial No. PCT/US2006/060556 dated May 10, 2008 (5 pages).

International Search Report from PCT Application Serial No. PCT/US2007/060940 dated Jun. 29, 2007 (4 pages).

Written Opinion from PCT Application Serial No. PCT/US2007/060940 dated Jul. 30, 2008 (7 pages).

International Preliminary Report on Patentability from PCT Application Serial No. PCT/US2006/060556 dated May 14, 2008 (12 pages).

International Preliminary Report on Patentability from PCT Application Serial No. PCT/US2007/061021 dated Aug. 5, 2008 (9 pages).

International Preliminary Report on Patentability from PCT Application Serial No. PCT/US2007/060940 dated Aug. 5, 2008 (8 pages).

* cited by examiner

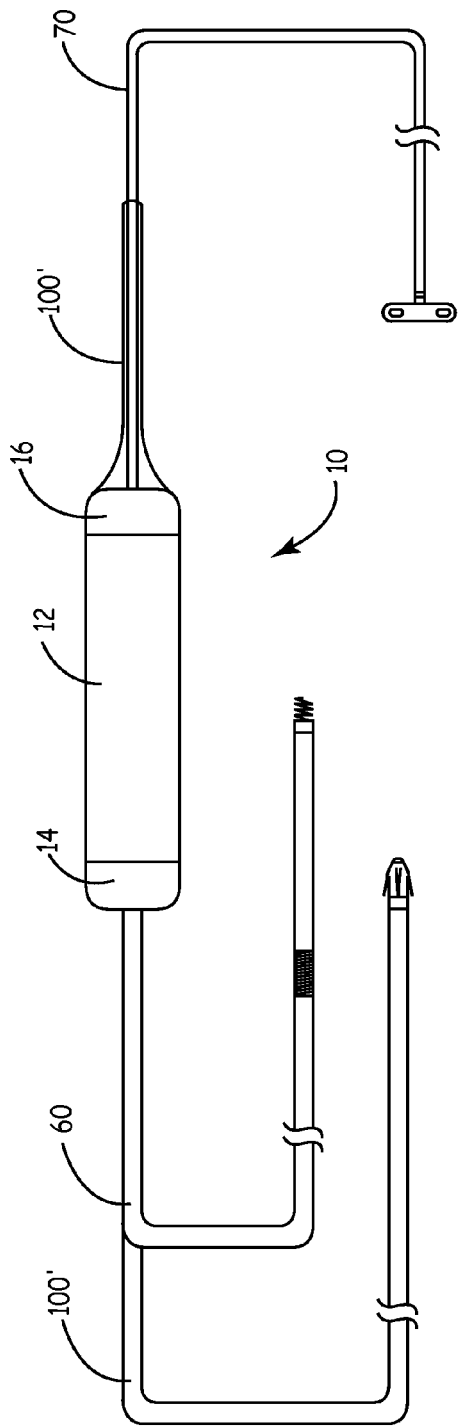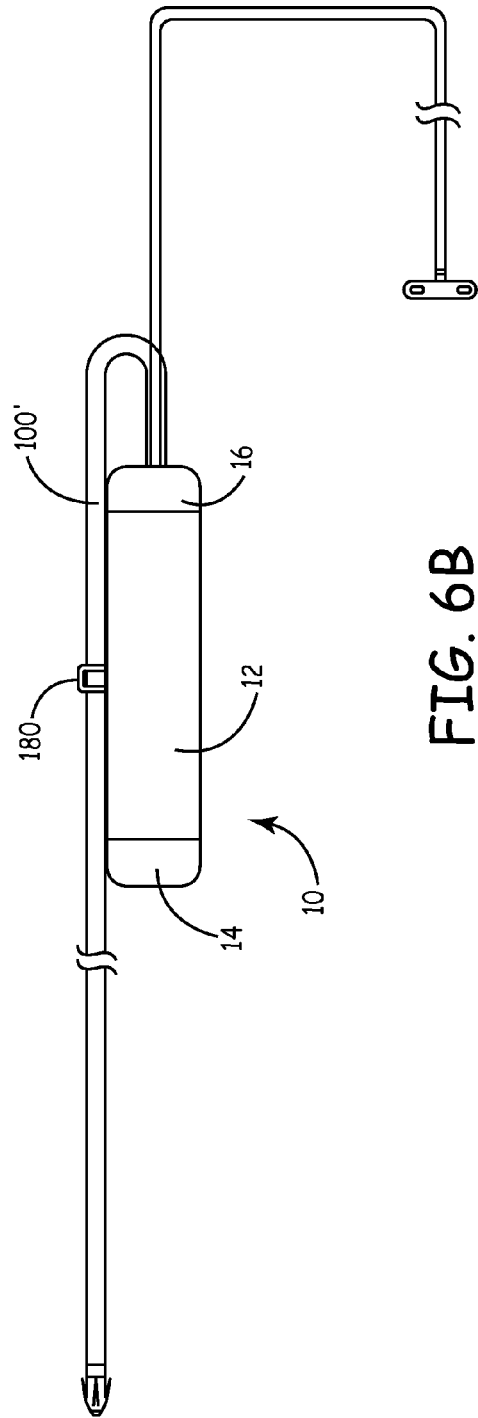
FIG. 6A
FIG. 6B

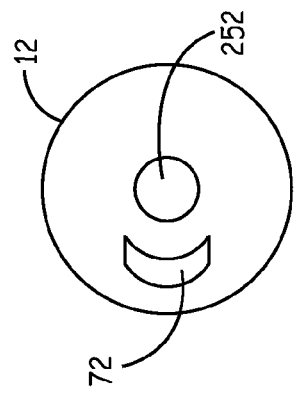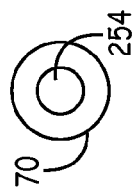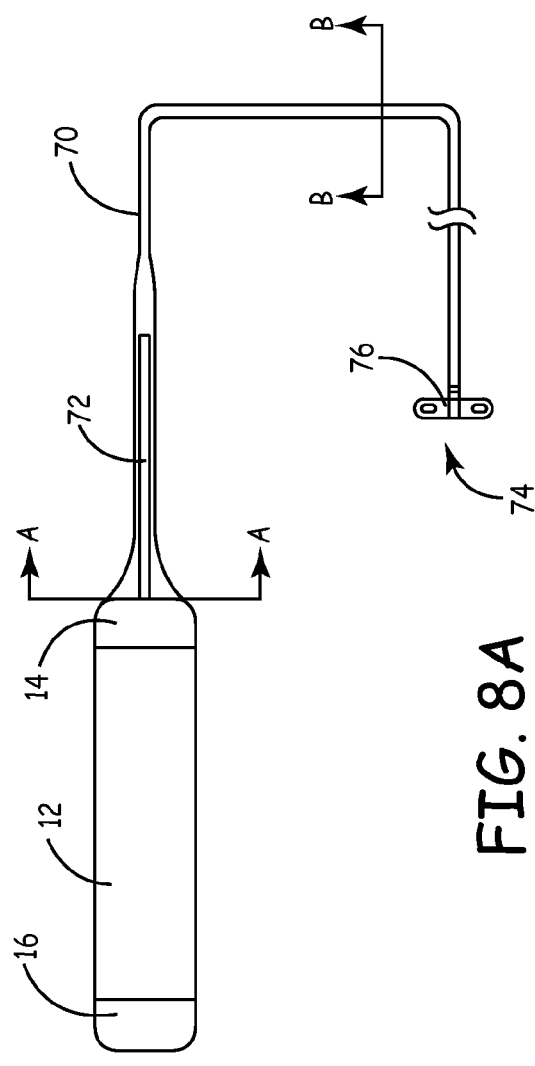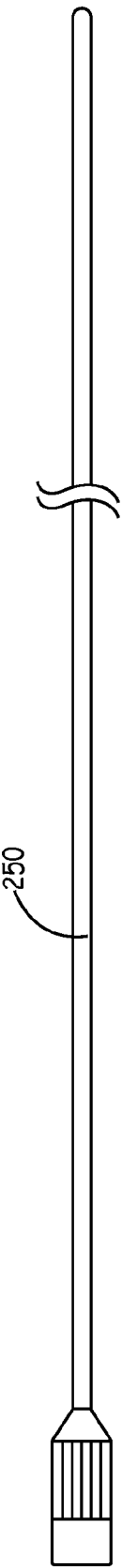

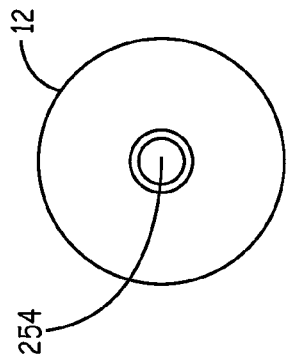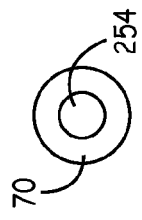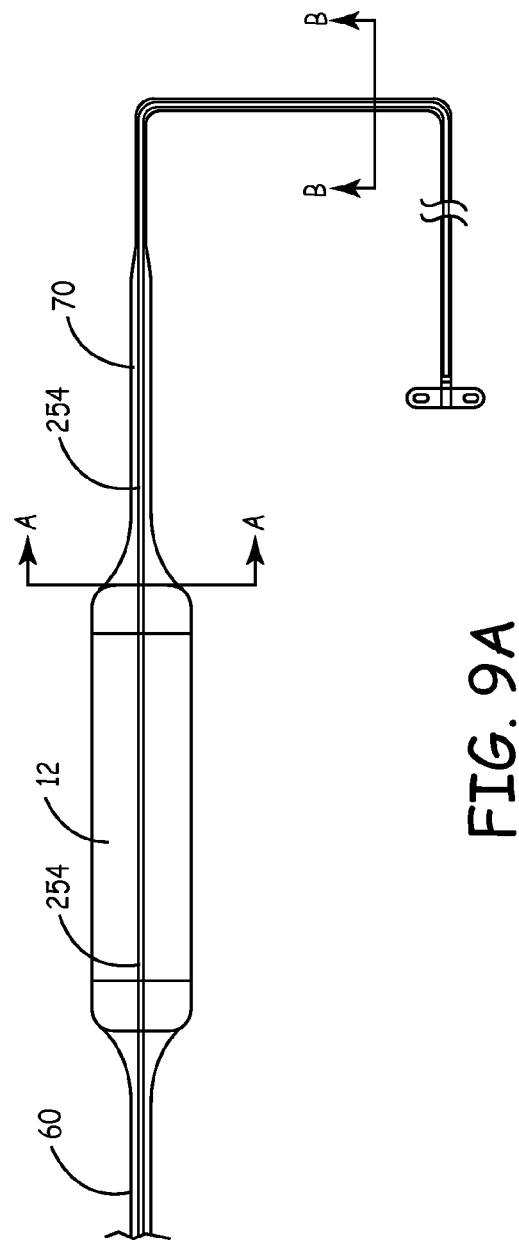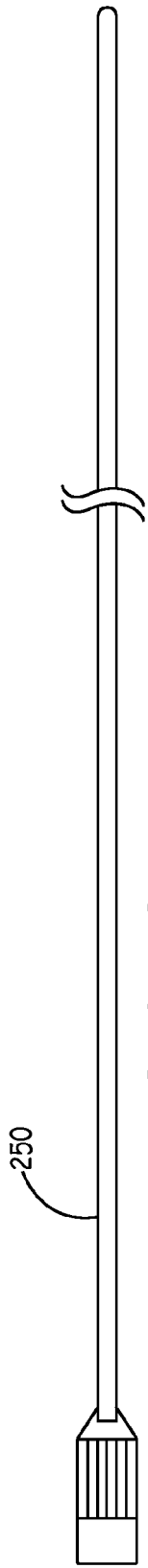

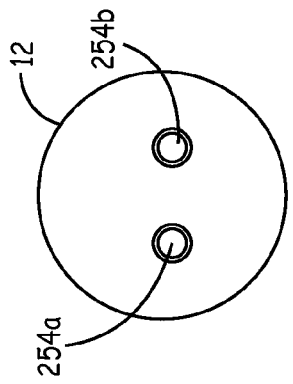
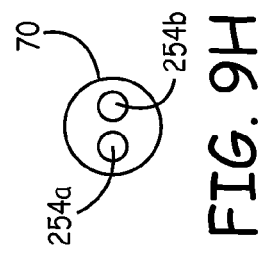
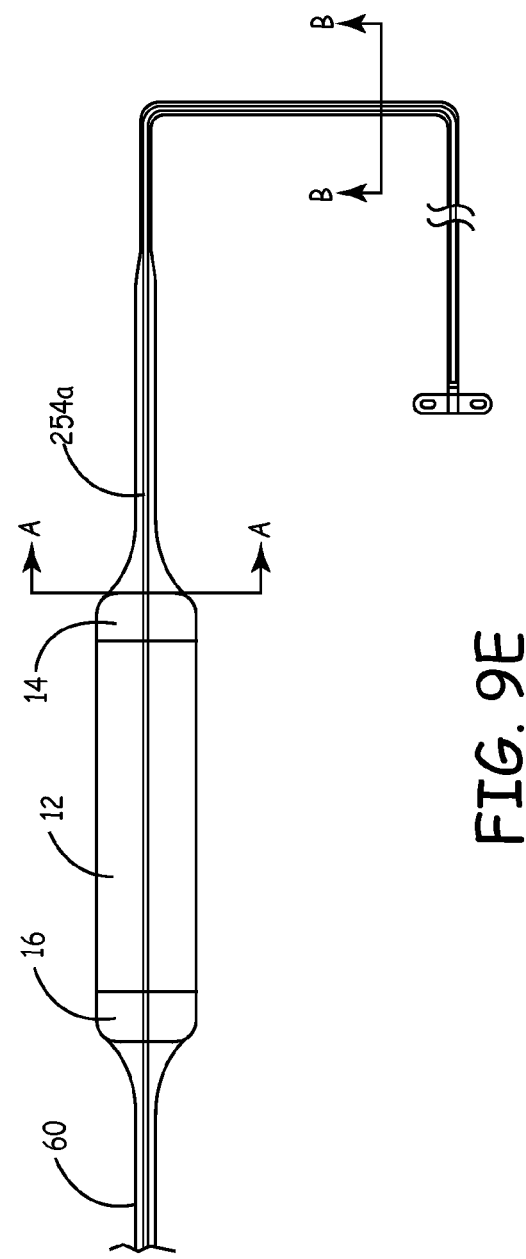
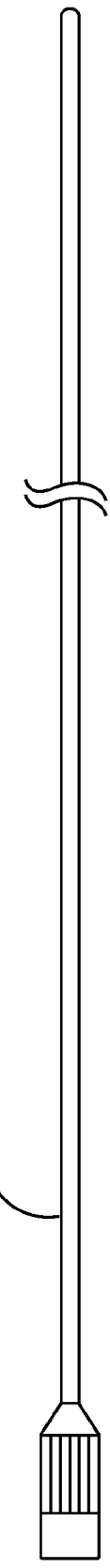

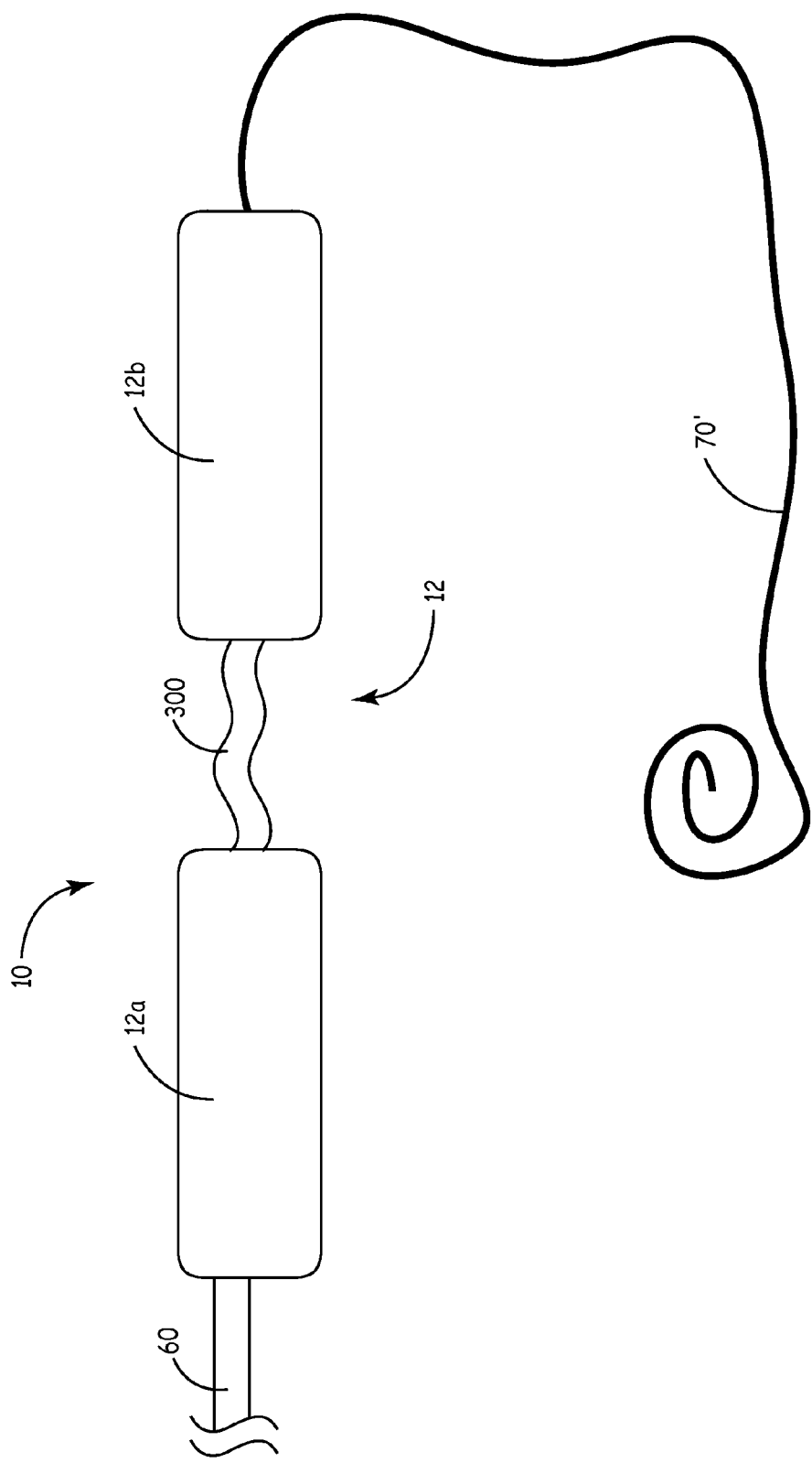

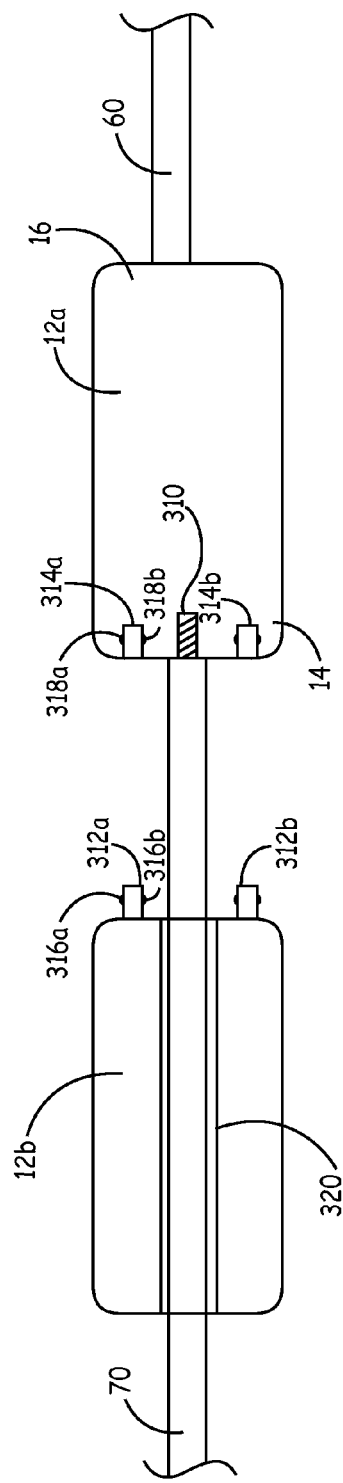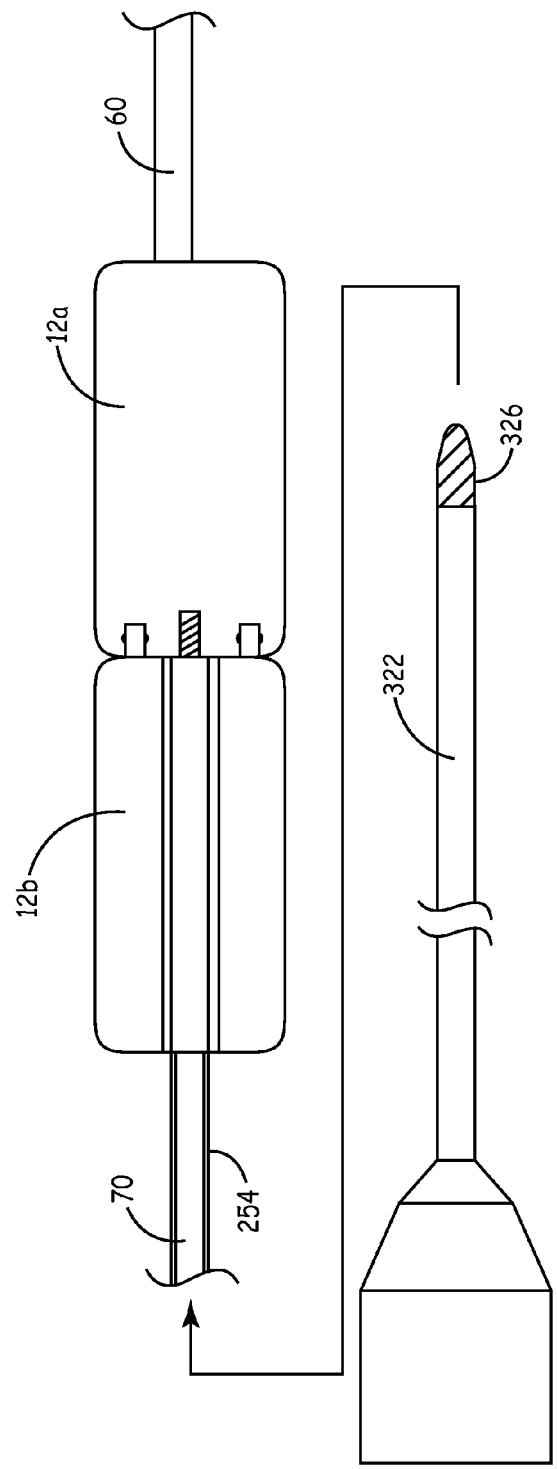
FIG. 11A
FIG. 11B

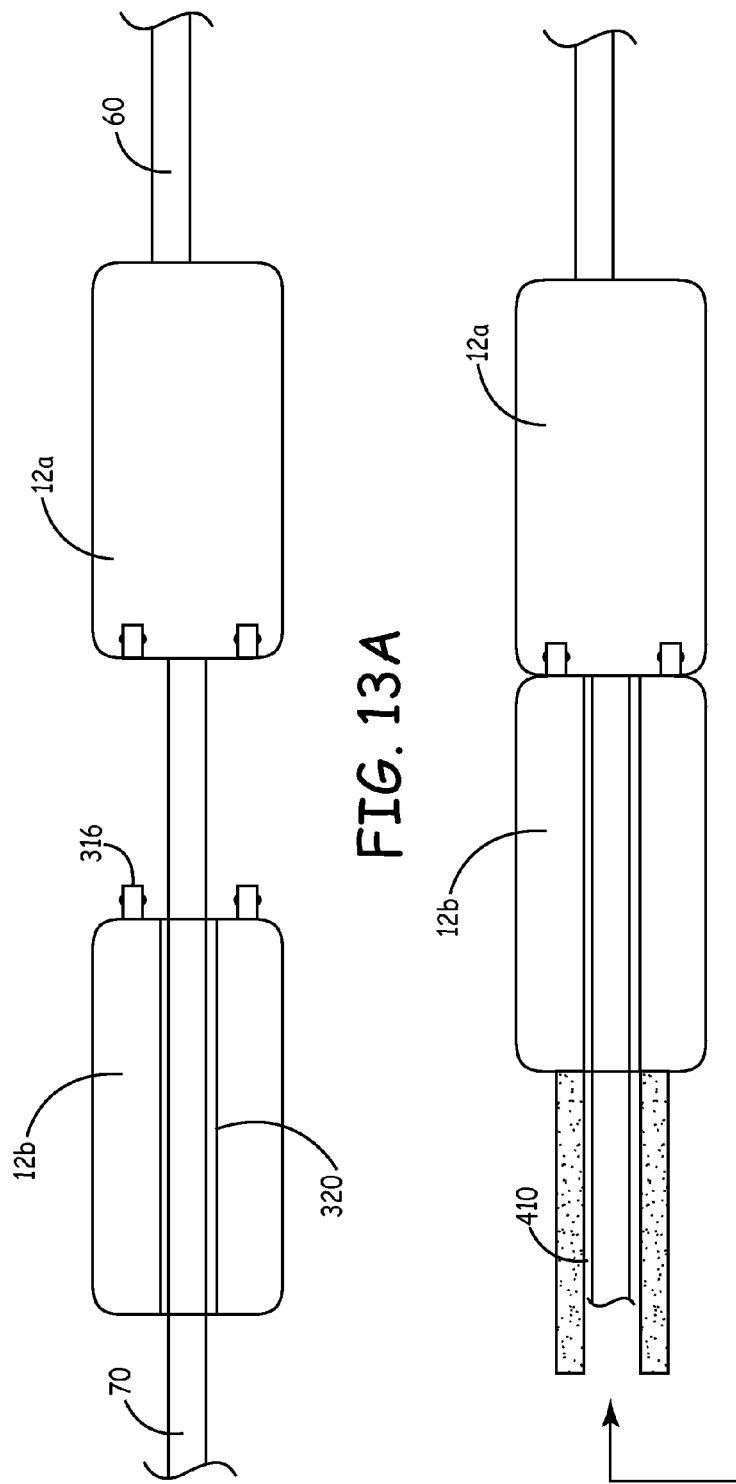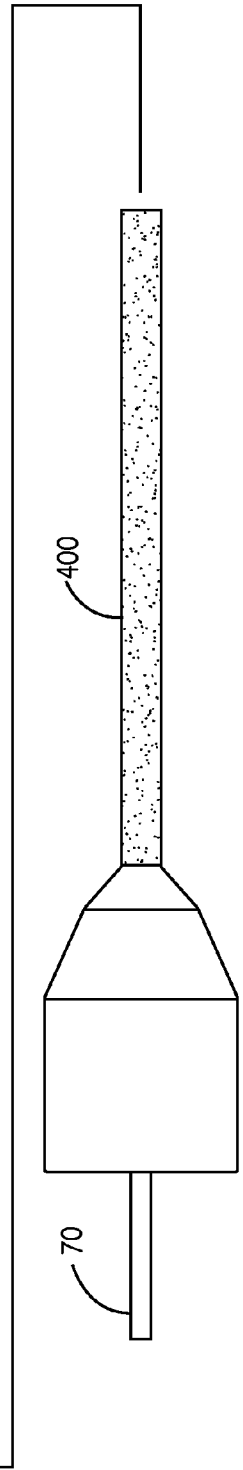

INTRAVASCULAR MEDICAL DEVICE

BACKGROUND

1. Field of the Invention

The present invention relates to medical devices and in particular, implantable medical devices.

2. Description of the Related Art

Medical devices related to managing, treating and providing therapy for cardiac conditions have changed and improved dramatically since their inception. Cardiac pacing, as an example, originally required an external pulse generator that itself required external power. While providing life sustaining therapy, patients were tethered to the power source and of course, power failures could prove catastrophic. Portable, battery powered external pulse generators were developed and provided the patient with the ability to be ambulatory; however, the pulse generator had to be carried by the patient. Furthermore, pacing leads were exposed through the patient's tissue and extreme care had to be exercised to minimize the risk of infection or inadvertent withdrawal.

Subsequently, fully implantable, battery powered pulse generators were provided in a hermetically sealed housing. This housing was rather large and was typically implanted in the abdomen of the patient, with leads extending to the heart. The size of such a device often made it rather uncomfortable and the implantation procedure was relatively invasive.

As technology improved, implantable medical devices (IMDs) have become continuously smaller, while offering increased longevity, reliability and many more features and therapies. Epicardial leads that were attached to an external wall of the heart were replaced with endocardial leads that are implanted transvenously, thus becoming minimally invasive. With these smaller devices, the housing was no longer placed in the abdomen but instead was implanted subcutaneously or sub-muscularly, often in the pectoral region. A "pocket" is formed underneath the skin or muscle sufficiently large to receive the housing of the IMD. The exposed or proximal ends of the leads are then connected to the housing and the incision is closed. While now routine, this is still a surgical procedure that requires skill and the appropriate medical facilities.

In general, patients are comfortable with these implanted devices and have a full range of motion, without interference or hindrance. Some patients feel the housing in the "pocket," which may be physically and/or psychologically uncomfortable. Physically, some patients may press against the housing during certain physical activities making the housing noticeable. Even if not a hindrance or painful, simply "feeling" the presence of the device may remind that patient that they have a medical implant and/or medical condition and this alone may be troubling to that patient. Some patients develop a habit of pressing against the pocket and hence against the IMD and often rotating or twisting the IMD. Typically, IMDs that have one or more leads will have any excess lead length coiled under (or around) the housing of the IMD. Thus, frequent patient manipulation may cause portions of the lead(s) to twist or rub, potentially damaging the lead body or pulling the lead out of contact with the targeted tissue. This is sometimes referred to as "twiddlers syndrome."

As the size and capability of IMDs has greatly improved, use of these devices has naturally expanded. This results in greater knowledge and acceptance among the patient population as well as within the medical community. As a result, caregivers are using IMDs with more frequency and for new and diverse purposes. For example, pacemakers are used in patients with various bradyarrhythmias. In such a patient, the heart's intrinsic pacing function fails or is deficient and the IMD provides electrical stimulation to maintain the proper heart rhythm. Such therapy is well known and is referred to above with the early, external pulse generators. Recently, the medical community has been using pacing technology in patient's whose heart rhythm is actually normal. Heart failure patients often have normal rhythm and conduction; however, this disease causes the heart to enlarge. As a result the left and right ventricles are unsynchronized when they contract even though the depolarization waveform triggering such a contraction was "timed" properly. Using cardiac resynchronization therapy (CRT), the left and right ventricles are paced, leading to a mechanical "resynchronization" of the left and right ventricular contractions. This not only leads to better immediate hemodynamic performance, but the heart itself often remodels itself (reducing in size) leading to an improvement in the disease state.

Not only are new therapies and treatments developing, implantable devices are now being used to collect sensor data for a variety of purposes. For example, implantable loop recorders (ILRs) are implanted subcutaneously and record cardiac data, unobtrusively, for extended periods of time. This allows robust medical data to be collected that, as a practical matter, may be otherwise unattainable.

These are merely two examples that illustrate the ever increasing trend to beneficially use implantable medical devices with greater frequency and for a wide variety of purposes that extend well beyond cardiac care. This presents a challenge to some caregivers who might want to use a given device for their patient but do not have the necessary surgical qualifications to actually implant the device. While such a patient may always be referred to another doctor, this adds cost and burden, some patients may not follow through, and some caregivers may simply opt for other treatments in order to maintain their relationship with the patient.

BRIEF DESCRIPTION OF THE DRAWINGS

FIGS. 6A-6B illustrate an IVMD having a lead and the tether coupled to a common end of the housing.

FIGS. 8A-8D illustrate an IVMD having a tether with a lumen.

FIGS. 9A-9D illustrate an IVMD having a tether with a lumen coaxial with a lumen through the housing and an attached lead.

FIGS. 9E-9H illustrate multiple lumens.

FIG. 10 illustrates a housing having multiple housing portions.

FIGS. 11A-11B illustrate multiple housing components with a common tether.

FIGS. 13A 13B illustrate an IVMD with multiple housing portions.

DETAILED DESCRIPTION

Figure 1:
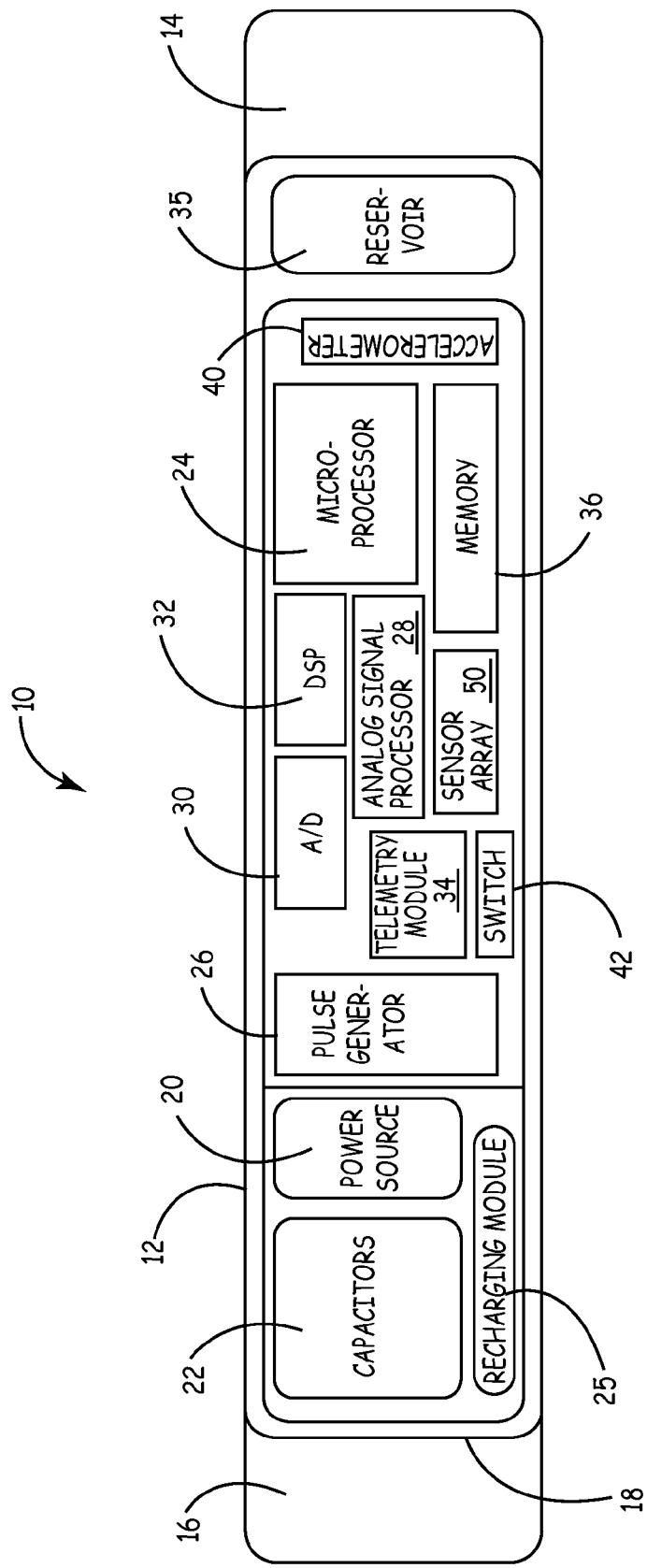
FIG. 1 is a schematic illustration of selected internal components of an intravascular medical device (IVMD) consistent with the teachings of the present invention.

FIG. 1 illustrates an exemplary intravascular medical device (IVMD) 10. The IVMD 10 is an implantable medical device that includes a hermetically sealed housing 12 containing components to control, power, and operate the device. The housing 12 is shaped and configured to reside entirely within the vasculature anatomy or within a given organ (e.g., the heart, lungs, kidney, pancreas, etc.) via the vasculature. In one embodiment, the housing 12 has an approximate diameter of 6-7 French. The IVMD 10 may have any number of functional areas including sensing, diagnostic, communications and therapy delivery. In the illustrated example, the IVMD 10 includes cardiac sensing, pacing and defibrillation as well as the ability to communicate with an external device through telemetry.

The housing 12 includes a proximal header 16 and a distal header 14. The operative components 18 include a power source 20, such as a battery. One or more capacitors 22 are provided that allow charge to be accumulated for rapid discharge to deliver a defibrillation or cardioversion pulse. A pulse generator 26 is coupled to the power source 20 and provides electrical stimuli for cardiac pacing.

A microprocessor 24, memory 36 (flash, EEPROM, ROM, RAM, DRAM, harddisk, etc.), analog to digital converter (A/D) 30, analog signal processor 28, and digital signal processor (DSP) 32 are positioned within the housing 12. An externally actuated switch 42 is provided and may take the form of a reed switch that is closed by a magnet. Such a switch 42 may be used to initiate a telemetry session with IVMD 10. Alternatively, communication may be initiated directly by an RF signal or other appropriate transmission medium. A telemetry module 34 provides the ability to transmit and receive data. A reservoir 35 is optionally included. The reservoir may provide a supply of a deliverable drug (e.g., insulin), genetic material, or biologic. The IVMD 10 may provide for the release of the material on a given schedule or based upon sensed need. Some materials, such as insulin, may be dispersed as needed but are predictably used; that is, the likelihood of delivery over a given time period is high. Other material may be delivered on an acute basis. For example, a dose of a blood thinner, coagulant, anti-coagulant, or adrenaline is provided and released when necessitated.

An accelerometer 40 may be utilized to provide an indication of patient activity for a rate response function and/or a relative position indicator; that is, physical position of the patient (e.g., prone). Finally, a sensor array 50 is illustrated. The sensor array 50 may sense any number of parameters such as temperature, pressure, velocity or other fluid flow characteristics, impedance, motion or size (e.g., ultrasound for wall motion and/or chamber size), oxygenation, glucose, or the level of any sensed chemical substance. It should be appreciated that while illustrated as contained within the housing 12, the sensor array 50 may have appropriate external portions not shown. For example, if used as a pressure sensor, a transducing membrane will form a part of housing 12 or part of a lead coupled with the housing 12, either physically or through telemetric connection (e.g., a body bus). Likewise, any additional component(s) for sensor array 50 will be included in this manner, as required. Cardiac data (e.g., electrogram (EGM)) will be sensed via one or more leads as explained below. In addition, the housing 12 may include one or more electrodes incorporated into the structure of the housing 12 (i.e., an active "can").

As indicated the power source 20 may be a single use battery. Alternatively, the battery may be rechargeable. As such, an optional recharging module 25 is illustrated. The recharging module 25 may receive power from an external source, such as directed RF energy, which is converted and used to recharge the battery 20. The RF energy may be collected via one or more antenna as discussed below, by using the housing 12 as an antenna, or by incorporating a receiver into the housing 12. Alternatively, or in addition, the recharging module 25 may use other mechanisms to generate power. In one embodiment, heat from within the patient is converted into current. In another embodiment, chemical energy from cells proximate the implant location is converted into electrical energy by the charging module 25. The charging module 25 may convert body motion into electrical energy. Such motion may come from multiple sources including without limitation gross patient movement (walking, exercising, etc.), lung motion (breathing), cardiac contractions, vasculature contraction (pulsitile blood flow), or fluid flow. The length of the unit provides the ability to harness mechanical power at one or more flexation points. Such flexation points may occur along the tether and/or in-between housing components. In this context, mechanical motion is converted into electrical energy by various mechanisms such as movement of a magnetic member within a coil. The charging module 25 may also used photovoltaic conversion to generate electrical current. A light collected placed sufficiently close to the surface of the patient's tissue will receive enough ambient light to provide power. Various other techniques are available to recharge the battery and are considered to be within the spirit and scope of the present invention. The following documents are herein incorporated by reference in their entirety: U.S. Pat. No. 6,242,827, issued to Wolf et al. on Jun. 5, 2001; U.S. Pat. No. 6,768,246, issued to Pelrine et al. on Jul. 27, 2004; US Published Application 2004/0073267, published on Apr. 15, 2004; and US Published Application 2004/0158294 published on Aug. 12, 2004.

The module 25 has been described in conjunction with a traditional Rechargeable battery 20 as a mechanism to recharge that battery. It should be appreciated that to conserve space, the traditional battery 20 may be eliminated or greatly reduced in size (due to a decrease in reliance upon the battery). That is, the various mechanisms described to generate electrical energy from sources around the IVMD 10 may be used to directly power the IVMD 10, without first storing that energy in a battery. This concept is applicable to any of the various forms the IVMD 10. In one embodiment, providing power directly from module 25 is utilized when the IVMD has low or minimal power consumption requirements (e.g., periodic sensing). Thus, power is generated for internal operations and when communication is desired, external power is provided for e.g., telemetry functions, through inductive coupling or RF power transmission. Of course, the IVMD 10 may be completely dependant upon such power conversion for all of its functionality. Finally, as indicated, a smaller battery or capacitor may be provided to collect some amount of energy prior to use; either to mitigate against fluctuation in the source (e.g., movement stops for a period of time) or to provide an even power supply to mitigate against power fluctuations; that is, to provide a relatively stable DC source.

Figure 2:
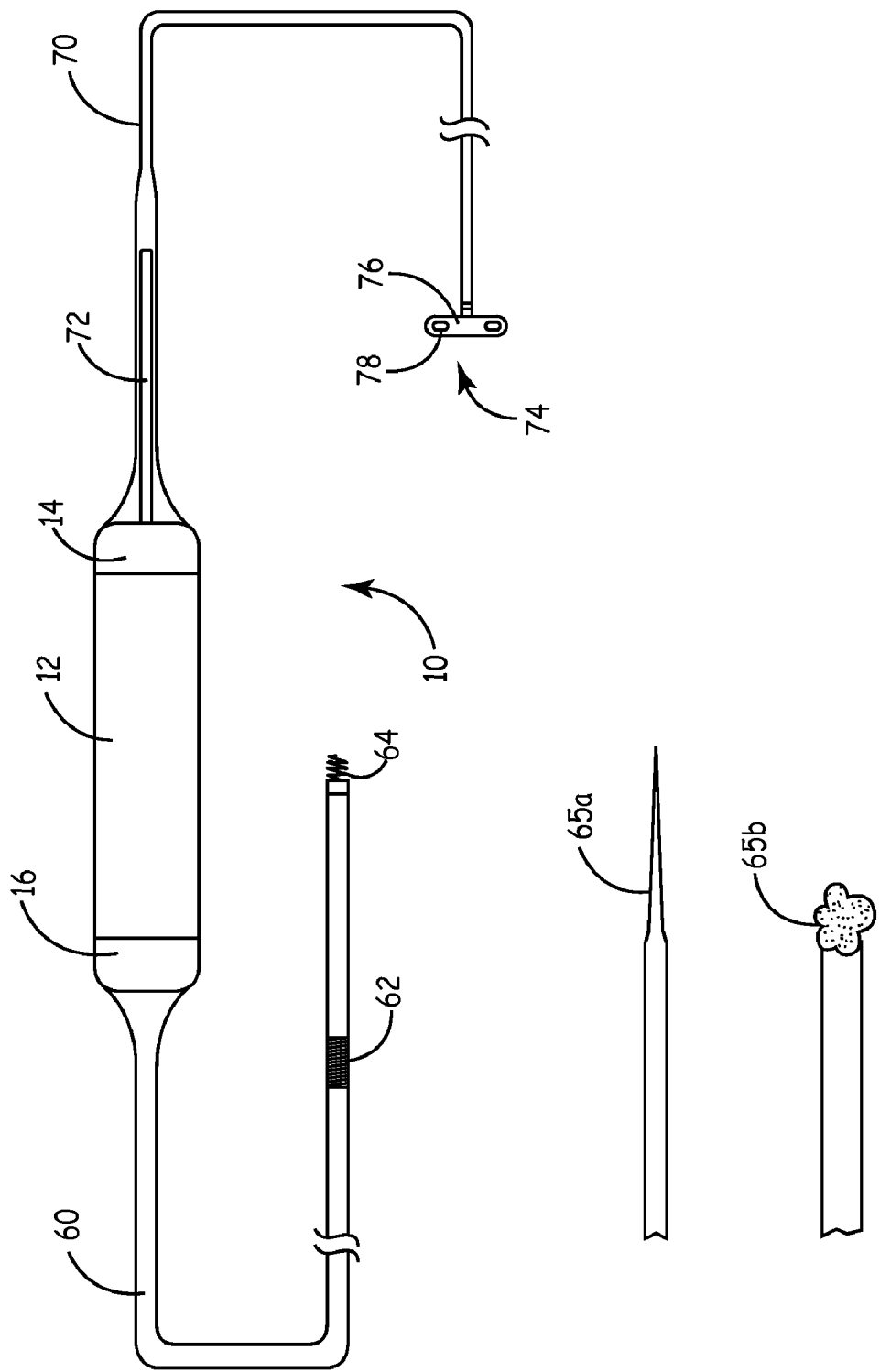
FIG. 2 is a schematic illustration of the IVMD including a tether and a lead.

FIG. 2 illustrates a lead 60 coupled with the distal header 16. One or more electrodes are incorporated into the lead 60. As illustrated, lead 60 includes a helical affixation member 64 that allows penetration into tissue to secure the distal portion of the lead 60 at a specific site. The helical affixation member 64 may serve as an electrode and/or the distal end of the lead 60, proximal to the helical member 64, acts as an electrode. A coil electrode 62 is positioned proximal to the distal end of the lead 60 so that when implanted, the coil electrode creates a defibrillation vector through an appropriate cardiac path with another electrode of the IVMD 10. The length of the lead 60 and the relative position of the electrodes are selected based upon the type of therapies, sensing and diagnostics provided and the implant location of the housing 12. The lead 60 may have other functions instead of or in addition to electrical stimulation or sensing. For example, a number of non-electrical parameters (e.g., pressure, temperature, velocity, chemical presence/concentration, etc.) may be sensed by providing an appropriate sensor. The lead 60 may have a delivery device to deliver drugs, genetic material, or biologics from the reservoir 35. Such a delivery device may include a needle 65a for delivery into tissue; a disbursing tip 65b (e.g., a porous surface for release into a fluid supply or against a larger surface area); or a variety of other delivery mechanisms.

The lead 60 is connected to the distal header 16. The connection may be a permanent, integral formation. That is, the lead 60 and housing 12 are fabricated to form an integral unit or the lead 60 is permanently affixed to the housing 12. Alternatively, the lead 60 is separable from the housing 12, as explained below. As used throughout, the designations proximal and distal header 14, 16 are used to indicate particular portions of the housing 12. It should be appreciated, that these portions may include a header in the traditional sense of an implantable medical device. That is, a separate portion from the remainder of the housing that includes various connection mechanisms (e.g., for receiving a lead connector pin). Alternatively, the terminology may simply refer to a given end or portion of the housing 12 to facilitate description.

A flexible tether 70 extends from and is securely coupled to the proximal header 14. At a proximal end 74, the tether 70 has an anchoring point. In the illustrated embodiment, a T-shaped anchor member 76 is attached to the tether 70 at the anchoring point. The anchor member 76 includes one or more suture ports 78 extending through the member 76. As indicated, IVMD 10 is implanted transvenously and the entire housing 12 resides within the vasculature or within an organ accessed via the vasculature. The tether 70 extends from the implanted location of the housing 12, through the vasculature and is anchored at or near the vasculature incision or puncture created for implantation. Thus, the tether 70 will fully or partially maintain the position of the IVMD 10. For example, if implanted in the superior vena cava, with a pacing lead 60 extending from the housing 12 into a cardiac chamber, blood flow and gravity (generally) will provide force against the housing 12 in a direction towards the heart. With the anchor point fixed, the housing 12 is prevented from traveling towards the heart and is thus secured. While suturing has been discussed, other methods of attaching or anchoring the tether 70 and/or the anchor 76 may be utilized.

The anchoring point 74 allows for subsequent identification and access to the IVMD 10. That is, if the IVMD is replaced or modified, the anchoring point 74 is located and the IVMD 10 can be accessed or removed via the tether 70 along the same vasculature pathway. As such, the anchoring point 74 may optionally include a radiopaque marker, may be constructed of a biocompatible metal, or having other identifying mechanisms to aid in determining the location of the anchor point 74 at a later time via X-ray, MRI, or other imaging techniques. Alternatively, the anchor point 74 may be positioned sufficiently close to the surface of the patient's skin that its location may be felt by applying pressure to the area.

The tether 70 is intended to secure the position of the IVMD 10 during the life of the implant. Accordingly, the tether material is constructed of a suitably strong, flexible, biocompatible material. The length of the tether 70 may include a drug eluting surface along the entire exterior, a portion of the exterior, or multiple distinct drug eluting surfaces may be provided. In some embodiments, the tether 70 may be used to temporarily secure the IVMD 10 until another anchoring mechanism is enacted (e.g., fibrotic growth). In yet another alternative embodiment, the IVMD 10 is intended to degrade within the body or pass harmlessly out of the body. For example, IVMD 10 may be a chemical sensor and the tether 70 secures the IVMD 10 at an appropriate location within the vasculature, counteracting the forces of pulsitile blood flow. Eventually, the sensor will dissolve and in such an embodiment, the tether 70 could likewise dissolve. Of course, the tether 70 provides a convenient mechanism to remove any such device thus providing for temporary implantation of a variety of medical devices, including pacemakers and defibrillators.

The tether 70 is provided with an excess length. After implantation of the lead 60 and housing 12, the desired length of tether 70 is determined. This final length should include enough excess to allow for normal movement of the housing 12 within the vasculature as well as any variations that will occur due to patient movement, positioning, growth or other physiological variations. The tether 70 is then cut at the appropriate location and anchored into place. The T-shaped anchor member 76, if used, is attached to the cut tether 70, either by suturing, mechanically clamping or using any other secure coupling mechanism.

As indicated, excess tether length is provided at the proximal end of the tether 70 with an expectation that this excess will trimmed or remain unused. This allows for flexibility during implantation and minimizes the need to have multiple pre-configured devices to accommodate different patient sizes and implant locations. Conversely, a distal portion of the tether 70 will reliably remain intact. Thus, this portion of the tether 70 may be used to provide additional structure or functionality.

As illustrated in FIG. 2, an antenna 72 extends from the housing 12 and may be contained within or affixed to an outer portion of the tether 70. Including the antenna 72 within the tether 70 provides a hermitic enclosure for the antenna 72 and any exposed feedthrough. The length, size, shape and configuration of the antenna 72 may vary from the illustrated embodiment and may extend for a relatively long length as compared to traditional implantable medical devices.

The antenna 72 may be used for communication and/or as an RF collector to receive power to recharge the power source 20. Furthermore, while one antenna structure 72 is illustrated, multiple antennas may be provided to facilitate different types of communication; to have a different antenna for transmission versus reception; to provide a separate power collector, to provide low and high power communication formats, to provide redundancy or for any number of reasons. One or more antennas may also be included in the lead body 60.

Figure 3:
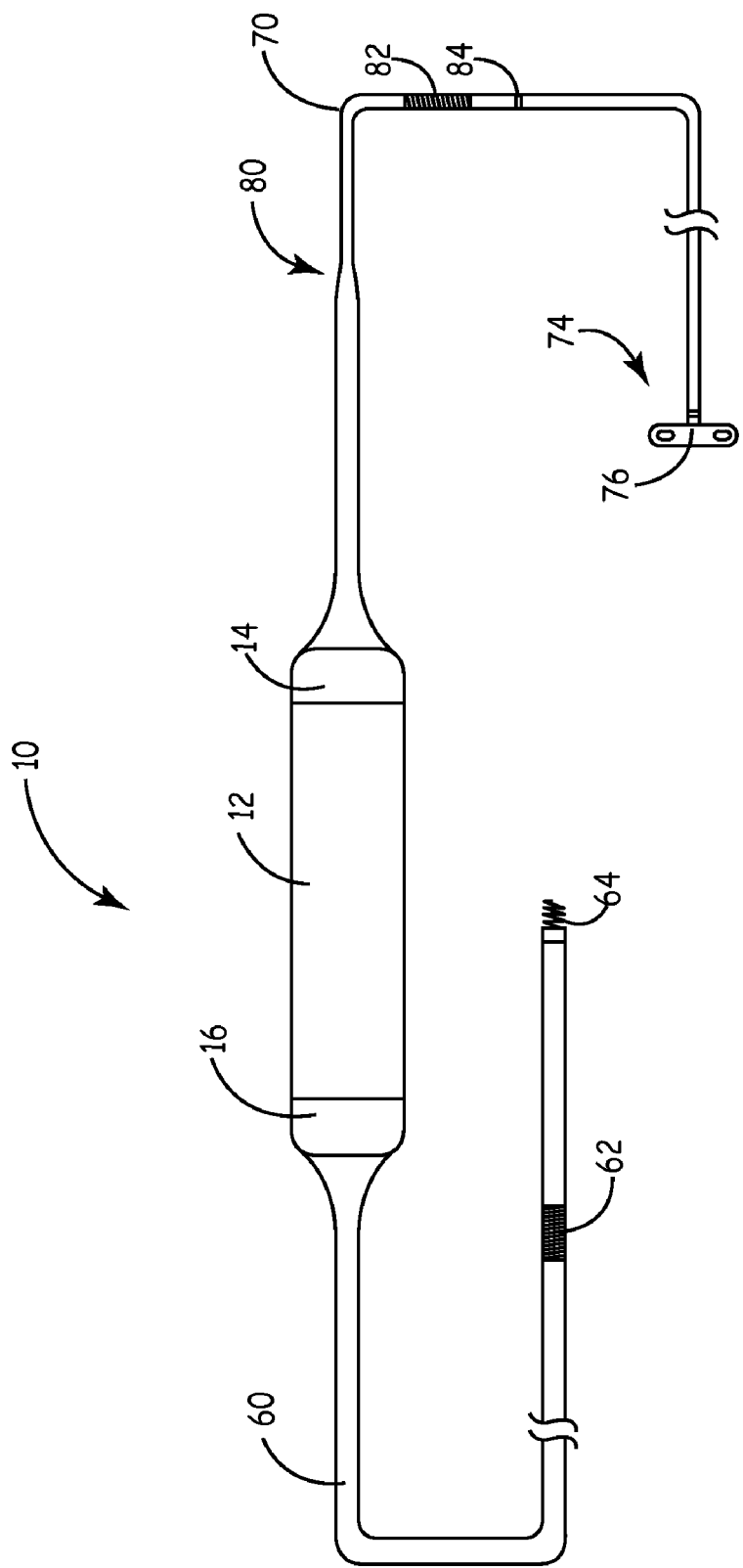
FIG. 3 illustrates an electrode incorporated into the tether.

FIG. 3 illustrates an alternative embodiment, wherein a distal portion 80 of the tether 70 functions as a lead having an electrode 82 for sensing or stimulation. That is, the electrode 82 is electrically coupled to the housing 12 via the distal portion 80 of the tether 70. This electrical coupling may be completely internal to and distinct from the tether 70 so that the mechanical properties of the tether 70 may be relied upon without adding stress or strain to what would be considered a lead body. The electrodes 62 and 82 may be positioned to facilitate defibrillation across the vector defined. In another embodiment, the electrode 82 acts as a pacing electrode. In yet another embodiment, element 82 is a sensor such as a pressure sensor. The antenna 72 of FIG. 2 is not illustrated, though such an antenna may also be provided when the tether 70 includes one or more electrodes and/or sensors. The structure of the tether 70 may vary over its length. The distal portion 80 is not intended to be severed. The proximal portion, in one embodiment, is intended to be severed; thus, a transition point 84 may be present. The tether 70 may have different materials and different construction from one portion to another or may have a unitary construction throughout.

Figure 4:
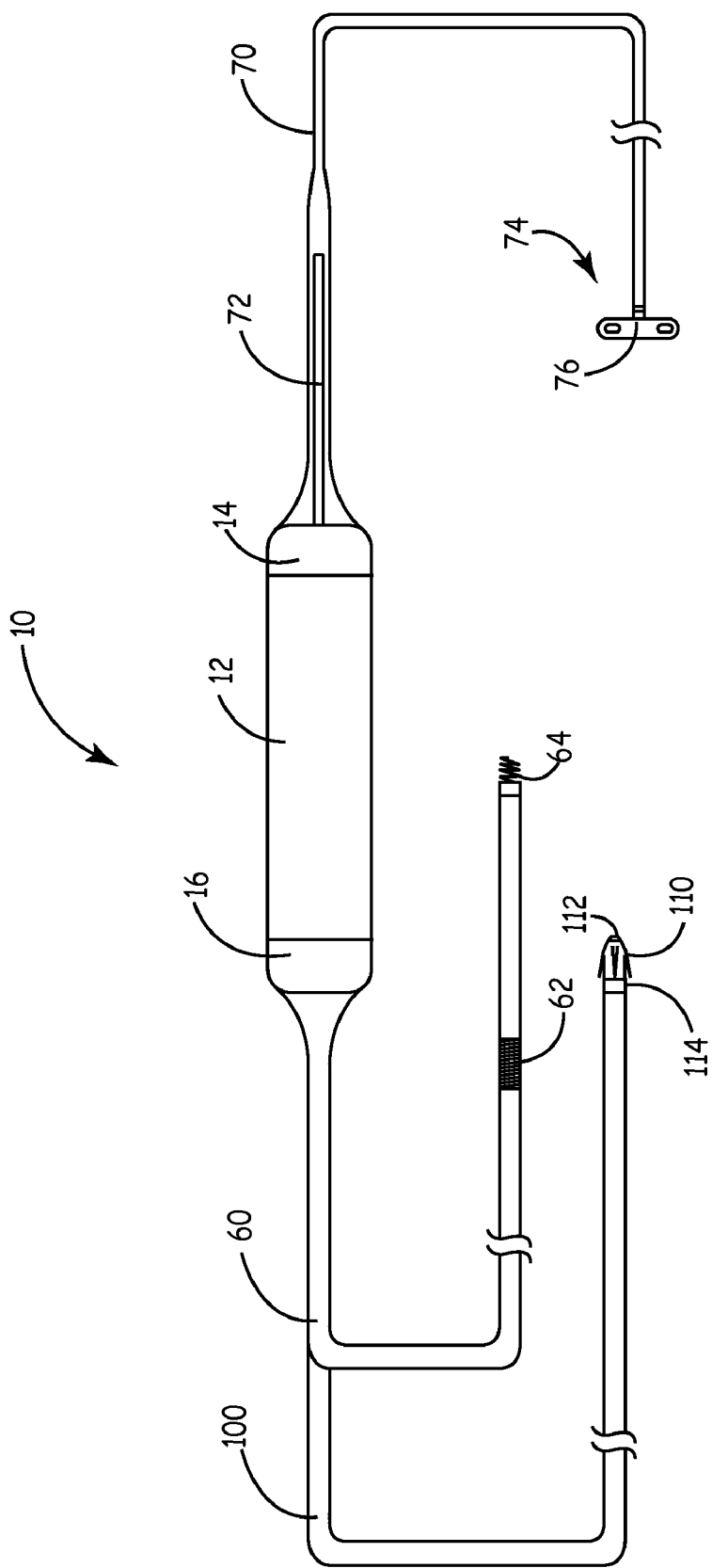
FIG. 4 illustrates an IVMD having multiple leads.

FIG. 4 illustrates an embodiment having lead 60 and lead 100 extending from the distal header 15. The second lead 100 is illustrated as having a tined tip 110 for securement as well as a tip electrode 112 and ring electrode 114. FIG. 4 is meant to illustrate that multiple leads may depend from the distal header 15 and a variety of electrode and attachment (e.g., tines, helical tip) configurations may be employed. The use of two such leads is not meant to be limiting and any number of additional leads may be provided. Though not illustrated, one or more additional electrodes may be present on tether 70, as illustrated in FIG. 3.

Figure 5:
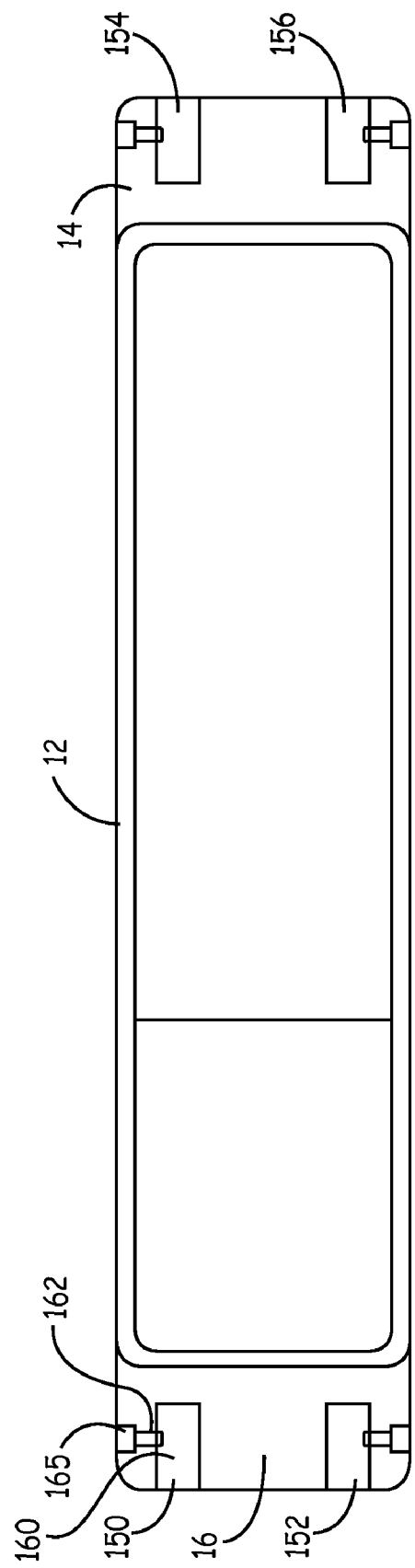
FIG. 5 is a sectional view of a housing of the IVMD.

FIG. 5 illustrates a sectional view of housing 12. In particular, multiple connection ports 150, 152,154 and 156 are illustrated in the proximal and distal headers 14, 16. Port 150 includes a cavity 160 shaped to receive a male connecting pin from, e.g., a lead. A set screw 162 is positioned to advance into the cavity 160 and engage the connecting pin, thus securing the pin in place. Access to the set screw 162 is gained through a set screw opening 165 that may include a self sealing material, such as silicone to reduce fluid entry into the set screw opening after implantation. The configuration of port 150 is repeated in each of the illustrated ports 152,154 and 156. More or fewer ports may be provided as necessary and alternative configurations may be employed. When used to received and secure a lead 60, the lead pin will make contact with one or more electrical connectors disposed within cavity 160. The tether 70 may also include a connector pin thus allowing for connection to the housing 12 in the same manner as a lead. Of course, if the tether 70 includes electrode(s), antennas or other components appropriate electrical contact is made via the pin and cavity. In the absence of such components, the tether is simply mechanically secured within the port 154,156. As indicated, the tether 70 may be integrally formed with the proximal header 14, thus appropriate access to ports 154,156 (if provided) is facilitated by the configuration of the tether 70 or by providing access through a portion of the tether 70.

FIGS. 6A and 6B illustrate an alternative multiple lead configuration. In this embodiment, lead 60 is coupled with the distal header 16. A second lead 100' is coupled with the proximal header 14 as is the tether 70. In some applications, it may be desirable to have the second lead 100' extend in the same direction as the tether 70, and as such, connection to the proximal header 14 is straightforward. Alternatively, and as illustrated, the lead 100' is extended in the same direction as the first lead 60 (i.e., distal to the housing 12). When coupled with the proximal header 14, the lead 100' is bent to achieve this configuration. While this is non-problematic for the lead 100', movement of the housing 12 via the tether 70 (e.g., retracting the housing 12) may be more difficult. To permit and facilitate such movement, the lead 100' is bent to provide sufficient excess so that the housing 12 may move relative to the lead 100' without affecting the tip placement. It should be appreciated the lead 60, extending from the distal header 16 also includes a certain amount of excess to address normal movement of housing 12 caused by pulsitile blood flow as well as some movement caused by withdrawal or retraction of the tether 70.

The curvature in the lead 100' may simply be imparted during implant, with the housing 12 remaining separate from the lead 100' other than at the proximal header 14. Alternatively, as illustrated in FIG. 6B, a guide member 180 may be provided on an outer portion of the housing 12. The lead 100' passes through the guide member 180 maintaining the lead 100' in close proximity to the housing despite the imparted curvature and any resulting bias. In addition, by appropriately sizing the guide member 180 and providing a material with a low coefficient of friction (e.g., parylene, silicone) on the guide member 180 and/or the lead 100', the housing 12 may be slid relative to the lead 100'.

For clarity, lead 60 is not shown in FIG. 6B. It should be appreciated that more than one lead may be coupled to the proximal header 14 in the manner illustrated. Furthermore, even if a single lead is employed, that lead may be coupled as illustrated by the lead 100' in FIGS. 6A and 6B. This would allow all connections to be made at one end of the housing 12 while still permitting lead advancement in a direction opposite to that of the tether 70.

Figure 7A:
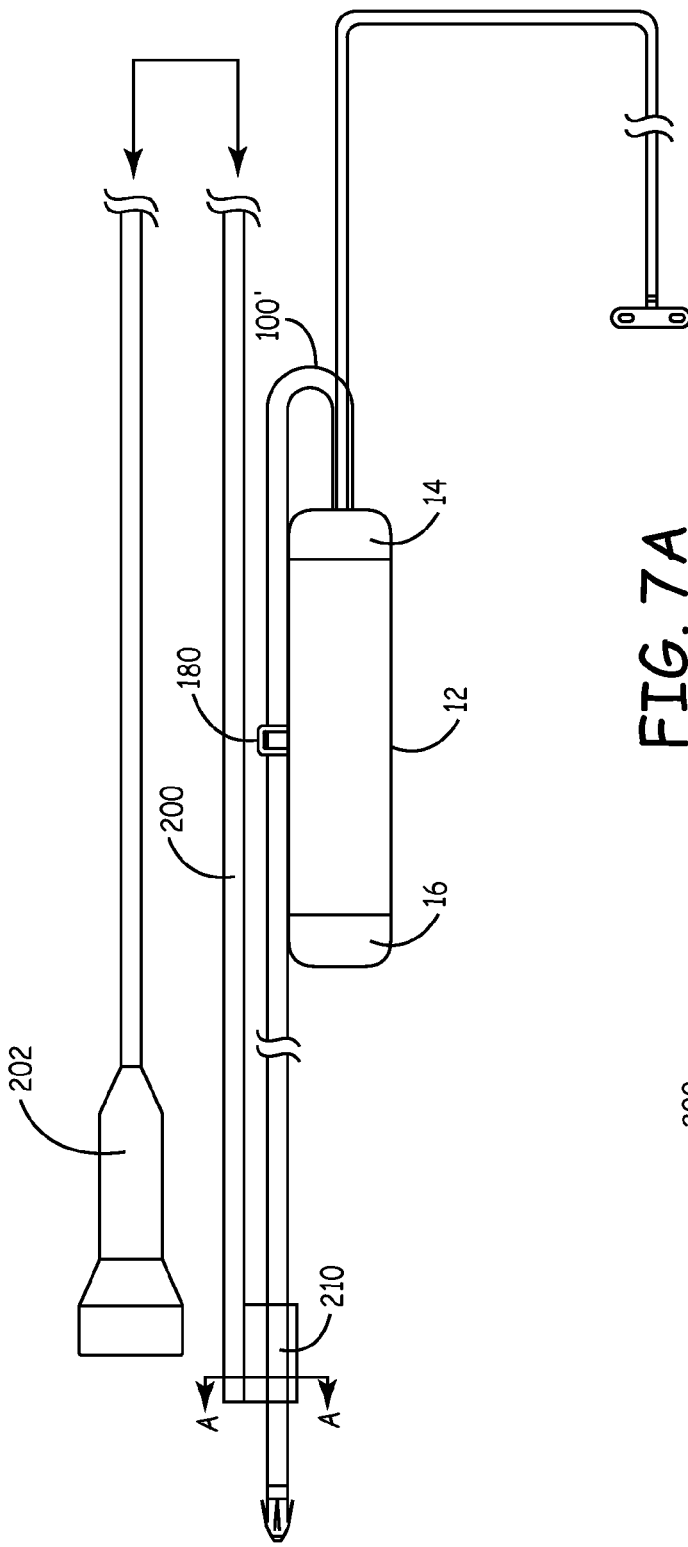
FIGS. 7A-7B illustrate a system for deploying the lead and housing.
Figure 7B:
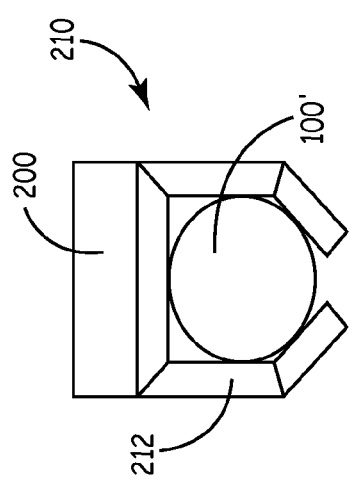

FIGS. 7A and 7B illustrate a system including a device that will aid in positioning any of the illustrated leads as well as the housing 12. A steerable stylet (or catheter) 200 has a handle portion 202 at a proximal end that includes controls that cause the stylet to flex or bend to facilitate intravascular navigation. A releasable clamping member 210 is positioned at or near a distal end of the stylet 200. The clamping member is illustrated schematically in FIG. 7B as a sectional taken about the line A-A of FIG. 7A. Upon actuation of the handle portion 202, the clamping member 210 opens and closes pivoting arms 212 so that lead 100' (or tether 70) is gripped or released. In this manner, the lead 100' is directed to a target location and the clamping member 210 is opened, releasing the lead 100'. It should be appreciated that the stylet 200 could be navigated as an over the wire catheter, thus following a previously positioned guidewire. The clamping of the lead 100' would remain the same; however, the stylet/catheter 200 would be guided by the guide wire as opposed to being navigated independently. As indicated, such a device may be used to position leads coupled with either the proximal head 14 or the distal header 16 and may be used to position the housing 12. To position the housing 12, the clamping member may be secured to a portion of an attached lead or to the tether 70. Implantation in this manner will be facilitated if the clamping occurs relatively close to the housing 12. Alternatively, a lead extending from the distal header 16 may be gripped at any position distal to the housing 12, so that advancement of the lead with stylet 200 advances the housing 12 as well.

FIGS. 8A-8D illustrate another embodiment wherein a steerable stylet 250 is used to position the housing 12. FIG.

8C is a sectional view taken about the line A-A in FIG. 8A and FIG. 8D is a sectional view taken about the line B-B in FIG. 8A. In this embodiment, the tether 70 has a lumen 254 sized to receive the stylet 250. While the T-anchor 76 is illustrated as being coupled with the tether 70, it should be appreciated that the T-anchor 76 may be attached afterwards and hence is not utilized with the stylet 250 or the T-anchor 76 includes a throughbore that aligns with the lumen 254, thereby permitting passage of the stylet 250. In this embodiment, an abutment 252 is provided on an exterior of the housing 12, as part of proximate header 14. Thus, as the stylet 250 extends through the lumen 254, the tip of the stylet 250 will eventually reach and strike the abutment 252. Continued advancement of the stylet 250 will cause advancement of the housing 12 within a vasculature pathway. If advanced too far, the tether 70 may be retracted, thus retracting the housing 12. As such, the housing 12 may be implanted at a target location by using the stylet 250 for forward advancement of the housing 12 and the tether 70 for any necessary retraction. Leads (not shown in these figures) may be implanted with the stylet 200 previously described or similar mechanisms, if utilized. FIG. 8C also illustrates how the antenna 72 (if included) is positioned outside of the path defined by lumen 254, which is congruent with abutment 252.

FIGS. 9A-9D are similar to FIGS. 8A-8D. In this embodiment, the lumen 254 extends through the housing 12 as well as the lead 60. Thus, the stylet 250 may be advanced all the way through the tether 70, the housing 12 and the lead 60 until it abuts an end of the lead 60. Thus, navigation of the stylet 250 will direct the distal end of e.g., lead 60 which pulls the housing 12, ultimately positioning that component as well.

FIGS. 9E-9H illustrate an embodiment having multiple lumens 254a, 254b through tether 70, housing 12 and lead(s) 60, with the second lead not illustrated. In this manner the stylet 250 can be directed through a specific lumen 254a, 254, to engage a particular lead separately from another lead. As should be apparent, more than two lumens 254a, 254b may be provided to permit more than two leads or other appendages to be directly manipulated by the stylet 250. Further, the size, spacing and configuration of the lumens 254 may be varied. In an alternative arrangement, more lumens are provided through the housing 12 and coupled with a corresponding lead than are provided through the tether 70. That is, the stylet 250 is directed through a lumen in the tether 70 and into a larger opening within the proximal header 14. The tip of the stylet 250 is then manipulated to manually select from a plurality of lumens each extending from this opening through the housing 12 to a particular lead.

While direct manipulation of the stylet 250 to select a desired lumen within the housing 12 is one option, alternative arrangements are available. For example, the tip of the stylet 250 may be sized or shaped to specifically engage only one lumen through the opening in the proximal header 14. For each such lumen engaged, the tip may be exchanged or a different stylet 250 may be utilized. As an example, the largest tip may be inserted through the common lumen in the tether 70 and will only access the largest sub-lumen passing through the housing 12. While occluding this larger opening, the next smaller tip may be utilized, and again a specific sub-lumen provides the only passage.

As described, the IVMD 10 may include multiple leads with each of these leads attached or coupled with the housing 12. Due to the size and implant location of IVMD 10, particular configuration of the housing 12 may make attachment of more than two leads cumbersome. In fact, in embodiments, the use of more than one lead may be cumbersome. In such a case, the present invention provides for the use of multiple IVMDs 10, each having one or two leads. The separate IVMDs 10 are in wireless communication so that their activities are synchronized. For example, one IVMD may provide atrial pacing and another may provide ventricular pacing. The multiple IVMDs 10 may be completely independent and simply communicate to one another to synchronize timing. Alternatively, one IVMD 10 may act to control the functions of one or more other IVMDs. The multiple IVMDs 10 may be implanted through the same entry point and reside in the same anatomical location or proximate one another (e.g., both within the superior vena cava but offset from one another). Alternatively, the multiple IVMDs may be implanted from different locations and reside remotely from one another, while retaining wireless communication.

FIG. 10 illustrates an embodiment wherein housing 12 is separated into two components 12a, 12b. The housing components 12a, 12b are operatively coupled together with a flexible interconnect 300, which may include one or more wires, cables or fibers for electrical or data communication. Alternatively, the flexible interconnect 300 may be a solely a mechanical coupling with each housing component 12a, 12b operating independently. For example, each may have separate functions. Alternatively, the housing components 12a, 12b are mechanically coupled and communicate in a wireless medium such as RF. Due to their close proximity, they may also be inductively coupled both for data communication and power transmission functions. Thus, the flexible interconnect 300 will mechanically connect the separate housing components 12a, 12b and may provide electrical, data and/or power couplings. As such, the flexible interconnect 300 will act like tether 70' as between housing component 12a and housing component 12b. That is, securing the proximal end of tether 70' will ultimately retrain housing component 12b through the flexible interconnect 300.

FIG. 10 also schematically illustrates a simplified tether 70' as compared to the tether 70 illustrated in previous embodiments. Simplified tether 70' is a generally linear, flexible member such as wire or cord and may be monofilament or multi-filar. The simplified tether 70' could be secured to an anchor member such as the T-anchor 76, which is then secured to tissue. Alternatively, the simplified tether 70' could be sutured directly to tissue.

FIGS. 11A and 11B illustrate another embodiment including multiple housing components 12a and 12b. As shown, housing component 12a includes the lead 60 extending from a distal end 16. The tether 70 extends in an opposite direction from the proximal end 14. A threaded receptacle 310 is axially aligned with a lumen 254 (FIGS. 8-9) through the tether 70. The second housing component 12b includes a through bore 320 sized to receive the tether 70. Thus, the housing component 12b may be added to or removed from the component 12a subsequent to implantation of component 12a.

The housing component 12a includes one or more receiving channels 314a, 314b that receive corresponding connector pins 312a, 312b. The engagement of connector pins 312 within channels 314 allows for a mechanical coupling as well as optionally providing for electrical connection through one or all of the connections. The connector pins 312 are provided with biased protrusions 316a, 316b received within detents 318a, 318b; thus, locking the connectors pins 312 into the channels 314 when full inserted. Initial insertion as well as subsequent release of the connector pins 312 may require retraction of the protrusions 316 internally via a mechanism that is not illustrated; thus, providing a secure locking mechanism. Alternatively, the spring bias of the protrusions 316 may be overcome by applying sufficient force in an axial direction. Thus, a locking action is formed that will maintain the connection of the two housing components 12a and 12b while implanted, but does not require additional components for engagement and/or disengagement. It should be appreciated that the size, shape, location, and configuration of the pins 312 and channels 314 may be varied in numerous ways while remaining within the spirit and scope of the present invention.

In FIG. 11B, housing component 12a is coupled with housing component 12b. Also illustrated is a stylet 322 having a threaded, tapered tip 326. The stylet 322 is inserted through the lumen 254 with the tether 70. The stylet 322 is advanced until the tip 326 reaches the threaded receptacle 310. Rotation of the stylet 322 then causes the threaded tip 326 to engage the receptacle 310. Once so engaged, linear movement of the stylet 322 will correspondingly move the housing component 12a (and 12b if coupled as illustrated). Furthermore, once fully engaged, rotation of the stylet 322 in a clockwise (with standard threading) direction will rotate the housing component 12a. Use of the stylet 322 in this manner allows for greater positional control of the housing 12a within the vasculature. While retraction of the tether 70 allows for gross movements, the engaged stylet 322 permits more precise movement which facilitates the attachment or detachment of housing component 12b, among other things.

In one embodiment, the stylet 322 is advanced through the tether 70 and threaded into the component 310. The housing receptacle 12b is then advanced over the tether 70 using another stylet (see e.g., FIG. 13B) to push the housing 12b. When the housing components 12a, 12b are proximate one another, stylet 322 is used (alone or in combination with tether 70) to hold housing component 12a in place and rotate housing component 12a to align with housing component 12b. When so aligned, the housing components 12a, 12b are joined. It should be appreciated that engagement mechanisms may be provided between housing member 12a, 12b that do not require specific alignment. That is, a retaining clip, channel or other member may extend about the circumference of the header of one housing component and a corresponding component may extend circumferentially (fully or partially) about the corresponding header of the other housing component; thus, relative rotational positioning between the two housing components is irrelevant to engagement so long as general axial alignment is provided. For example, rather than having channel 314 discretely receives a single pin 312, the channel 314 may extend circumferentially around the proximal planar face of the housing component 12a. Thus, the pin(s) 312 may be received anywhere along this channel 314. Relative rotation is permitted even when protrusions 316 and detent 318 (which may also be circumferential) are utilized. Alternatively, the detent(s) 318 may remain discrete and rotation of the housing components 12a, 12b will cause engagement.

Figure 12A:
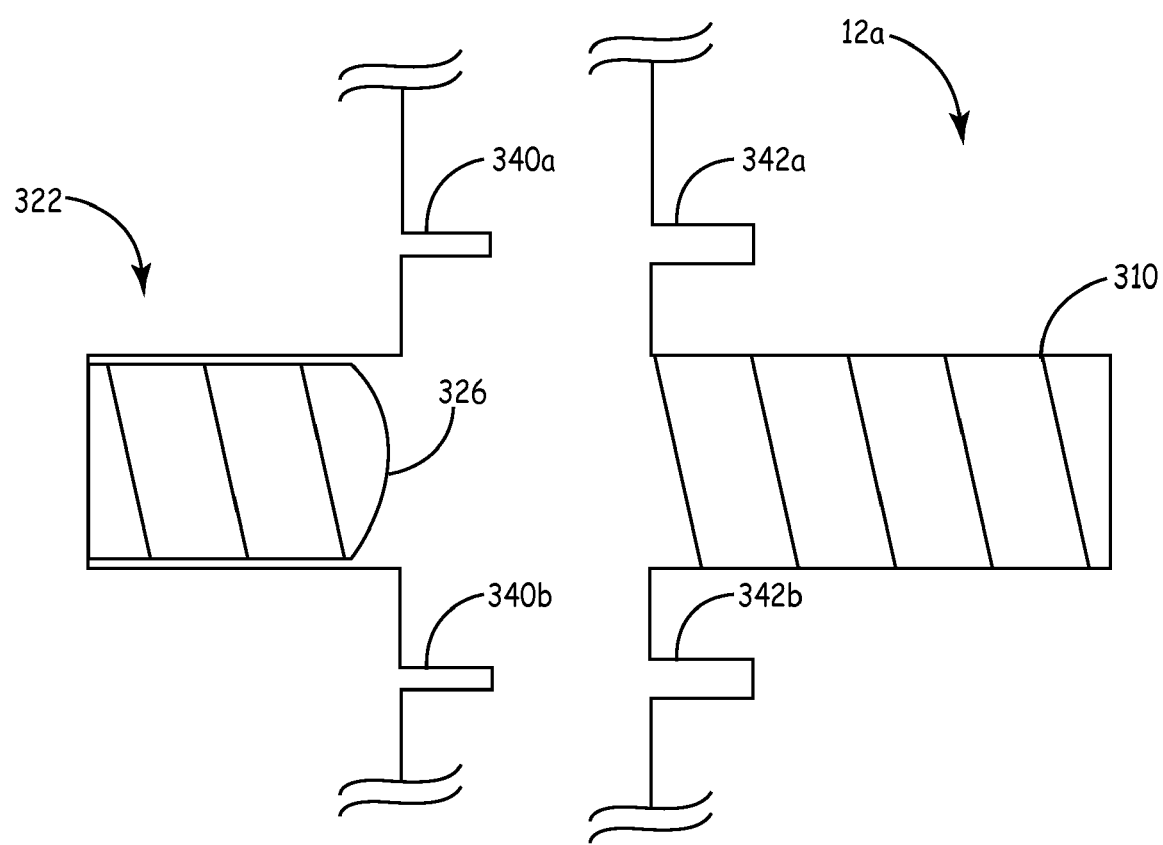
FIGS. 12A-12D illustrate a mechanism to attach a stylet to a housing component.
Figure 12B:
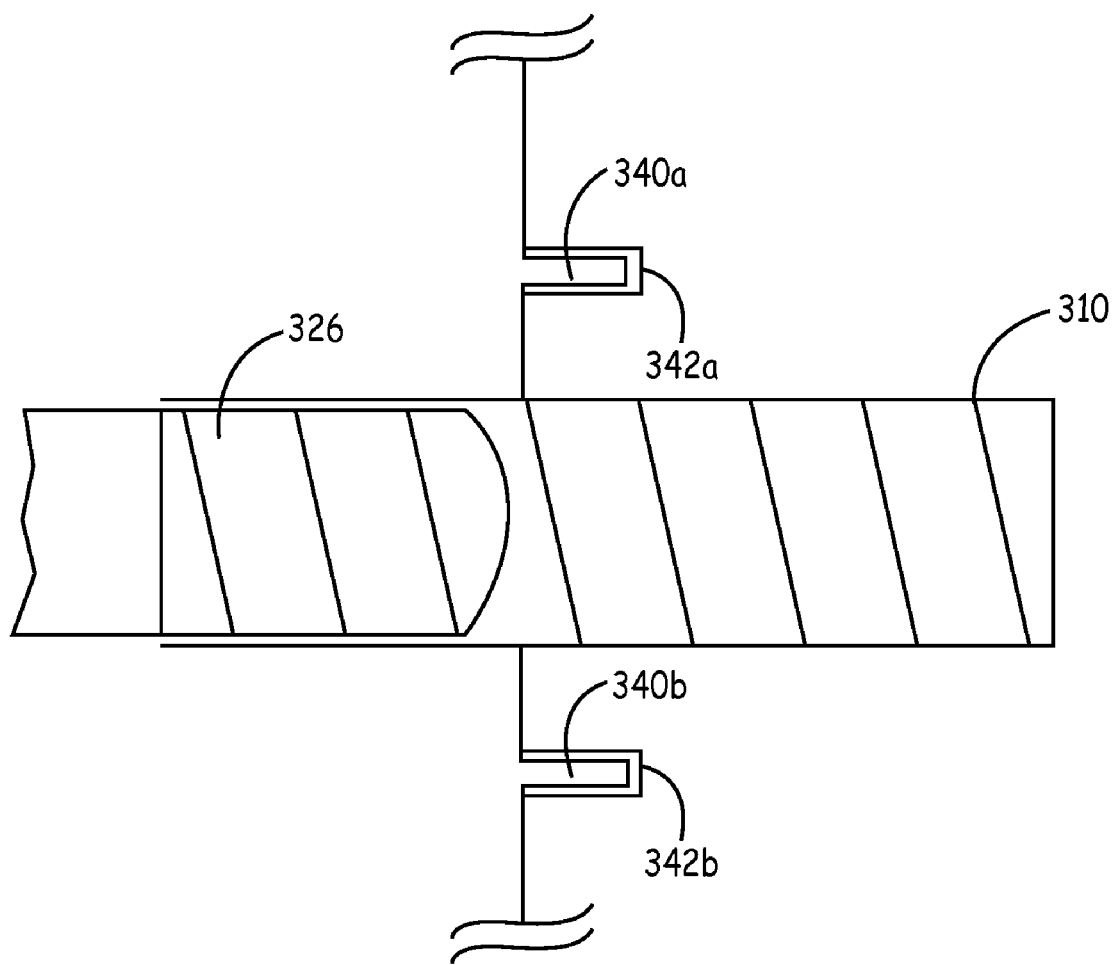
Figure 12C:
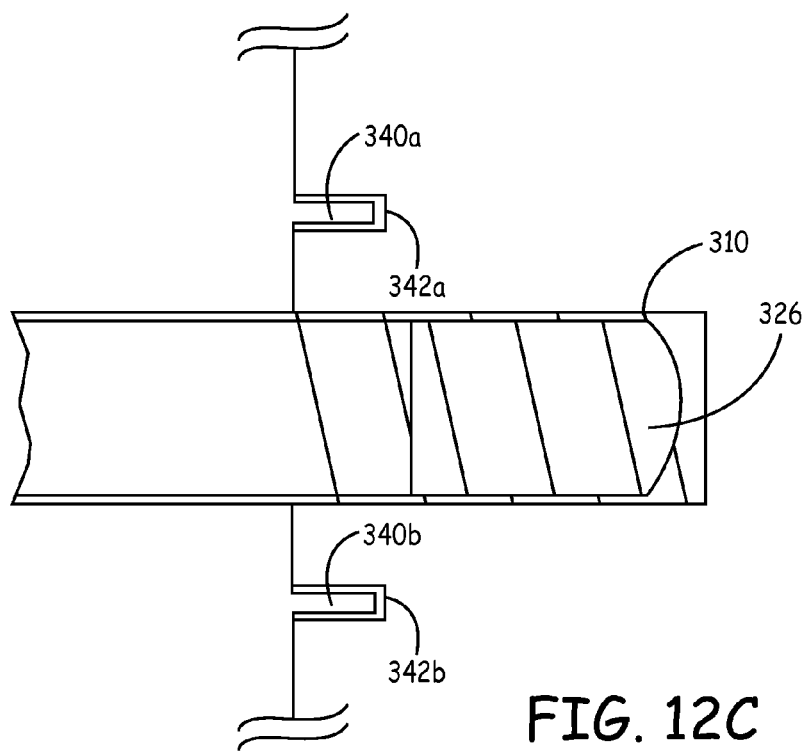

FIGS. 12A-12D illustrate another embodiment of stylet 322. FIGS. 12A -12C are side sectional views of a tip portion of the stylet 322. Initial engagement of the threaded tip 326 may be made more difficult since the housing component 12a is relatively free to rotate when implanted. The stylet 322 in the present embodiment includes an outer sheath 350 and an inner rod member 352. The threaded tapered tip 326 retracts and extends from the outer sheath 350.

Figure 12D:
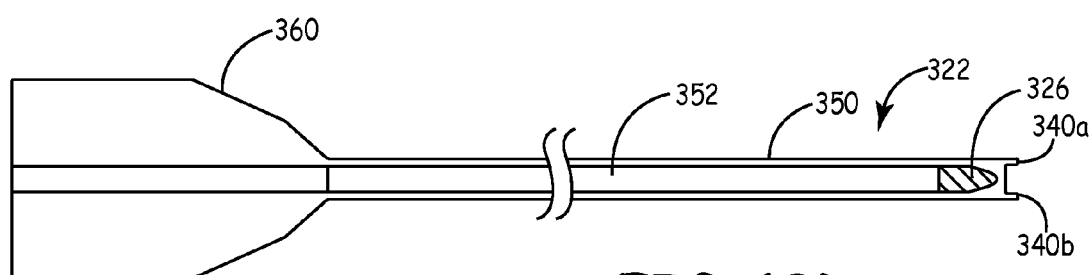

One or more pins 340 extend from the outer sheath 350, with two such pins 340a, 340b illustrated. The pins 340 are sized to easily engage openings 342 (with 342a and 342b illustrated). It should be appreciated that more openings 342 may be provided than pins 340 to again ease initial engagement. As illustrated in FIGS. 12A and 12D, the tip 326 is initially retracted within the sheath 350 and the stylet 322 is spaced from housing 12. The stylet 322 is advanced until the pins 340 engage the openings 342, as shown in FIG. 12B. Rotation of the stylet 322 may be necessary to achieve this engagement. Again, the fit of the pin 340 to the opening 342 need not be particularly tight. Subsequent rotation of the stylet 322 will cause the pins 340 to abut a surface of the openings 342. Subsequently, the rod 352 may be advanced via control at a handle 360 and rotated so that tip 326 is threaded into the receptacle 310, thus achieving a secure engagement so that subsequent manipulation of the stylet 322 will directly control the housing 12.

FIGS. 13A and 13B illustrate another embodiment utilizing multiple housing components 12a, 12b. In this embodiment, the tether 70 is coupled with housing component 12a and housing component 12b is slid over the tether 70. A stylet/catheter 400 is provided that includes a lumen 410 sized to receive the tether 70. Thus, the stylet 400 is also slid over tether 70 and is used to push housing component 12b into engagement with housing component 12a. Though not separately shown, it should be appreciated that the stylet 400 may be releasably secured to housing component 12b so that advancement, retraction and rotation of the housing component 12b is facilitated. The manner in which stylet 400 is releasably secured to housing component 12b may vary and may include without limitation any of the coupling arrangements discussed herein.

Figure 14:
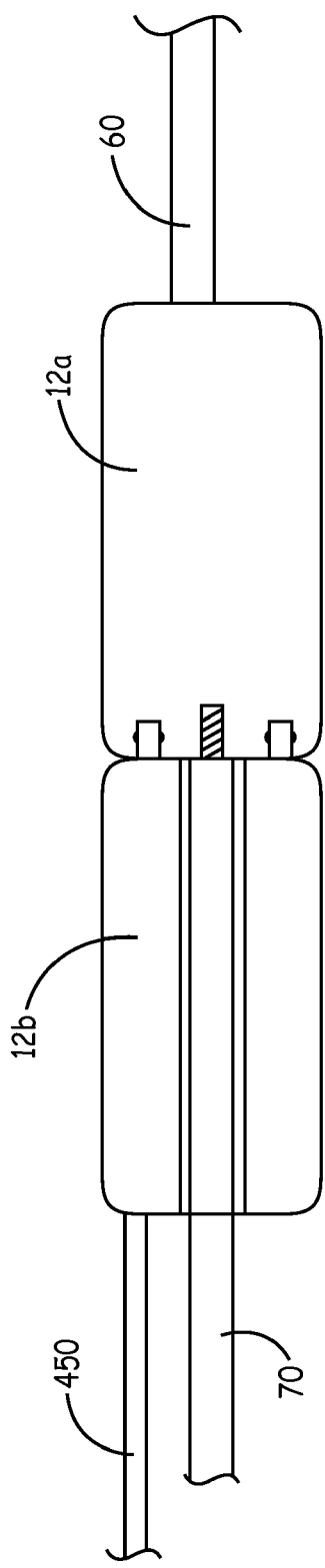
FIG. 14 illustrates an IVMD having multiple housing potions and multiple tethers.

FIG. 14 illustrates an embodiment of a multi component housing 12, wherein the distal housing component 12b includes a supplemental tether 450. The supplemental tether 450 may be permanent or temporary. In either case, the tether 450 may be used to retract housing component 12b while a device such as stylet 400 is used to advance the housing component 12b. When permanent, the supplemental tether 450 may be separately sutured at a distal end for securement or may simply be affixed to the tether 70.

Figure 15:
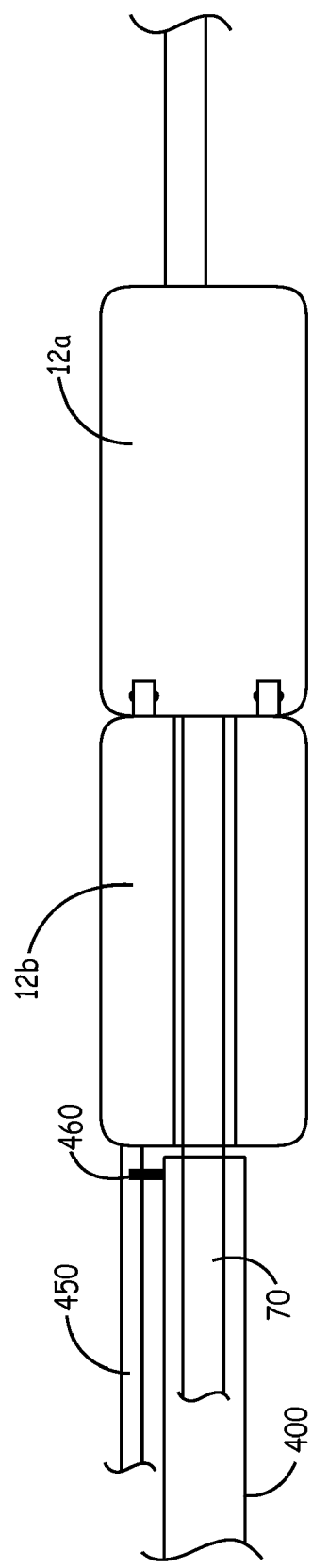
FIG. 15 illustrates an interaction of a stylet with both tethers of FIG. 14.

FIG. 15 is an embodiment similar to that of FIG. 14. In this embodiment, the stylet 400 includes an outwardly extending tab 460. As the stylet 400 is rotated (in either direction), the tab 460 will engage the secondary tether 450, causing the housing component 12b, to rotate with the stylet 400. Thus, the stylet 400 is used to advance and rotate the housing component 12b, without any other coupling required and the secondary tether 450 is used to retract the housing component 12b.

Figure 16:
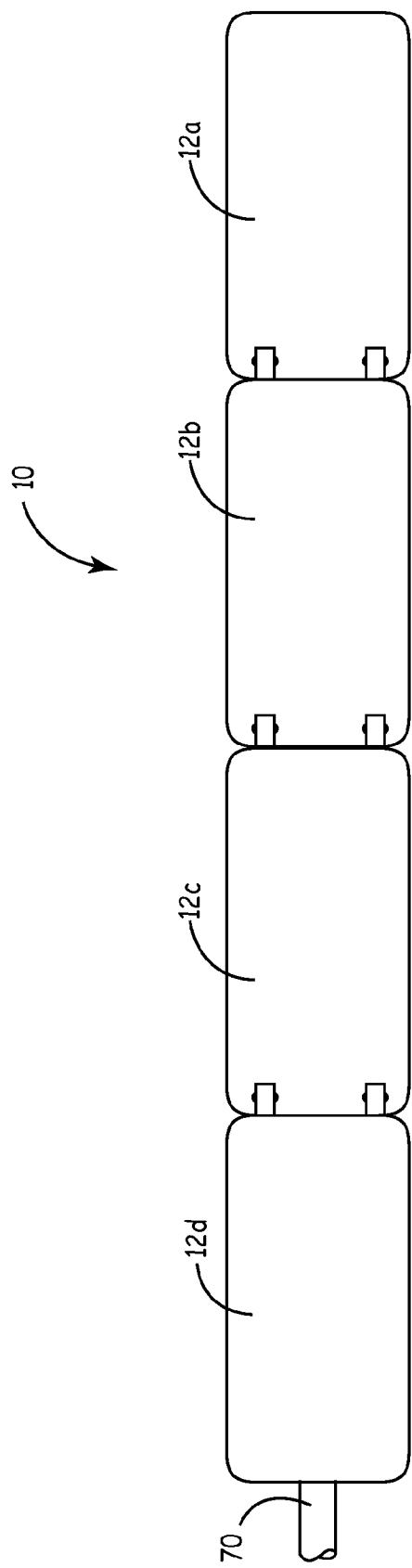
FIG. 16 illustrates an IVMD with multiple housing portions.

More than two housing components may be coupled together to form or modify the IVMD 10. As previously indicated, different parts of the same device may be separated between housing components. Alternatively or in addition, subsequent housing components may be added to provide additional therapies, diagnostics, capabilities or power. For example, an IVMD 10 may be implanted with a single use (i.e., non-rechargeable) battery. At a later point, another housing component may be added that includes a power supply to replace the depleted or soon to be depleted single use battery. Thus, the useful lifetime of a given device may be extended with a relatively minor procedure. An IVMD 10 may initially be implanted having pacing functions and a later module may be added that provides defibrillation therapies. FIG. 16 illustrates one embodiment of IVMD 10 having four joined housing components 12a, 12b, 12c and 12d. It should be appreciated that any number may be joined using any combination of the embodiments discussed herein. It should further be appreciated that each such component need not have the same size and shape. This will depend upon the components included in any given section of housing 12 and may take advantage of variations in the vasculature anatomy.

The IVMD 10 may also be accessed post implant to add components (as discussed above) or to exchange components. That is, rather than simply adding a housing component 12 having an additional battery 20, a housing portion 12 having the battery 20 is first removed over the tether 70 and a new housing portion 12 is added. In this manner, the lead(s) 60 may remain in place, while other portions of the device are removed, replaced or otherwise manipulated. To that end, it should be appreciated that the distal header 16 may take the form of a full or partial housing component 12 that remains in place and is tethered to allow other housing components to be manipulated. Alternatively, the tether 70 may be coupled with a distal portion of the lead(s) or lead connector. Thus, the entire housing 12 may be added/removed while the lead(s) remains implanted and tethered. Finally, it should be appreciated that the IVMD 10 may provide a variety of functions including sensing, diagnostics and/or therapy. Thus, accessing the IVMD 10 via the tether 70 allows for other components to be exchanged without removing the entirety of the device. For example, chemical sensors may become depleted of a source material or catalyst and replaced in this manner. Similarly, longer term drug eluting member or drug reservoirs may be replaced. Such reservoirs may contain traditional pharmaceuticals and/or genetic materials or biologics. The IMVD 10 may be used to deliver such agents (e.g., gene therapy) to a target tissue location. When necessary, the IVMD 10 is re-supplied without requiring complete extraction or the implantation of another device.

Figure 17:
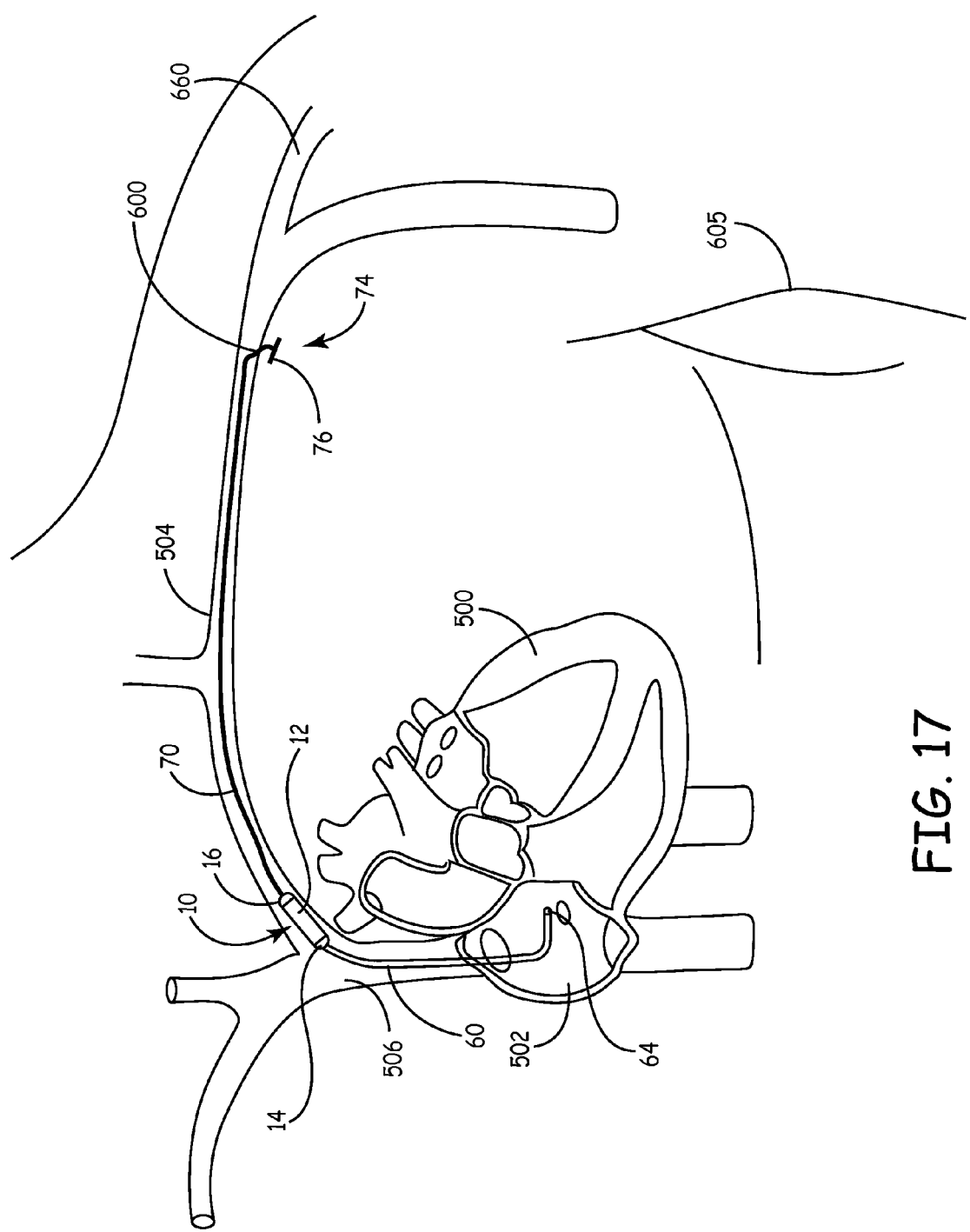
FIG. 17 illustrates an implanted IVMD.

FIG. 17 illustrates an IVMD 10 implanted within the subclavian vein 504 and extending into the superior vena cava 506 of a heart 500. The lead 60 is illustrated as being an atrial pacing lead and a distal tip 64 is affixed within the right atrium 502. Multiple additional leads may be included. The tether 70 extends from the proximal header 14 of the housing 12 through the subclavian vein 504. The proximal end 74 of the tether 70 exits the subclavian vein 504 at an initial entry point 600. The proximal end 74 is secured to tissue surrounding the initial entry point 600, by e.g., the T-shaped anchor 76 which is sutured to the tissue. As pulsitile blood flow, directed towards the heart 500, and patient movement will cause movement of the housing 12, a sufficient amount of slack material is provided along the length of the tether 70.

Figure 18:
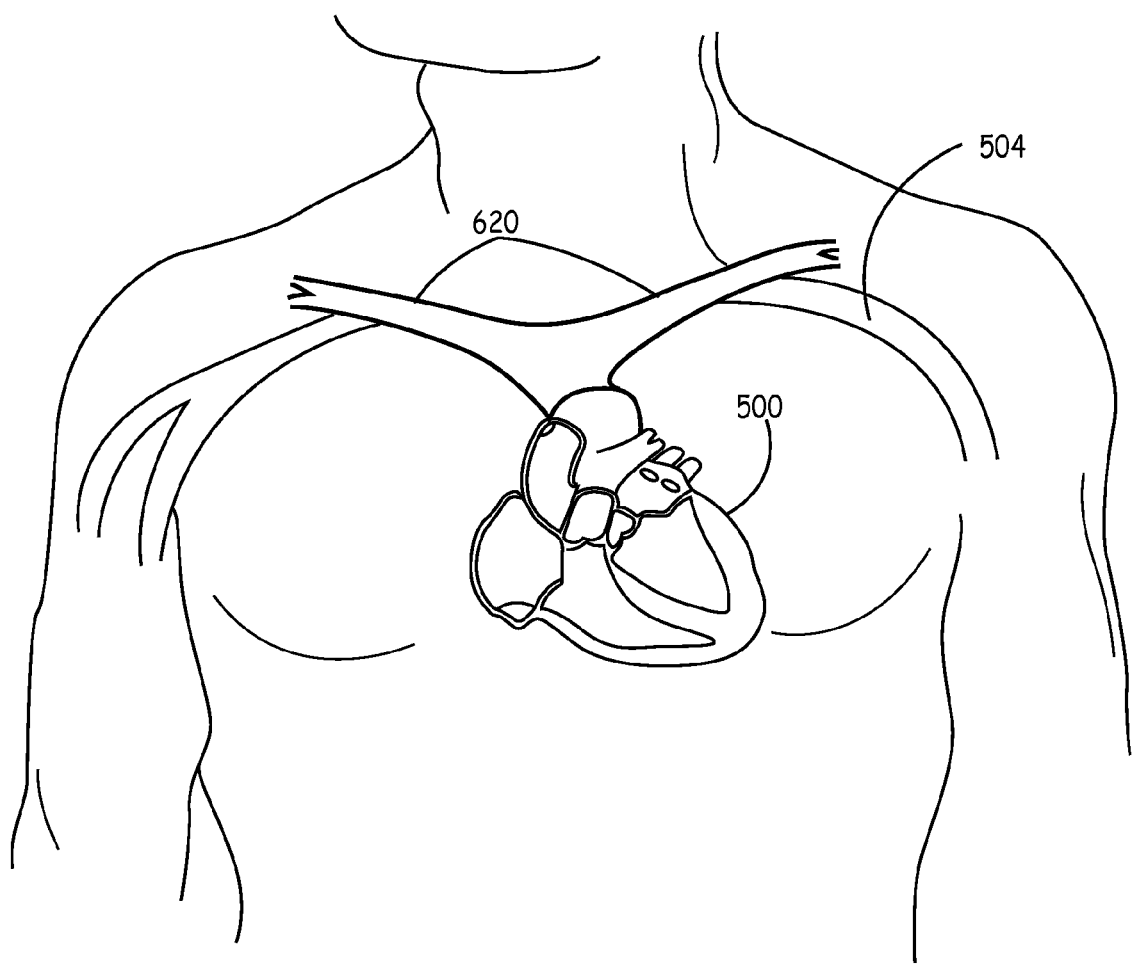
FIG. 18 illustrates the anatomical relationship between the subclavian vein and the clavicle.

The position of housing 12 illustrated in FIG. 17 is non-limiting. If desired, the housing 12 may be positioned closer to the initial entry point 600, thereby increasing the length of the lead 60. Conversely, the housing 12 may be positioned closer to or even within the heart 500, increasing the length of the tether 70 and decreasing the necessary length of the lead 60. FIG. 18 illustrates the position of the heart 500 relative to the subclavian vein 504 as well as the clavicle 620. In some embodiments, it may be desirable to position the housing 12 within the superior vena cava 506 below (towards the heart 500) the clavicle 620. This avoids any potential for "subclavian crush" wherein leads or components within the vasculature are compressed between the clavicle and the first rib (not illustrated). The size and nature of a given IVMD 10 will determine whether this is or is not a concern. Due to its size, shape and material properties, this will generally not affect the tether 70. Furthermore, implantation via the subclavian vein 504 is only one entry site and others may be utilized.

Figure 19:
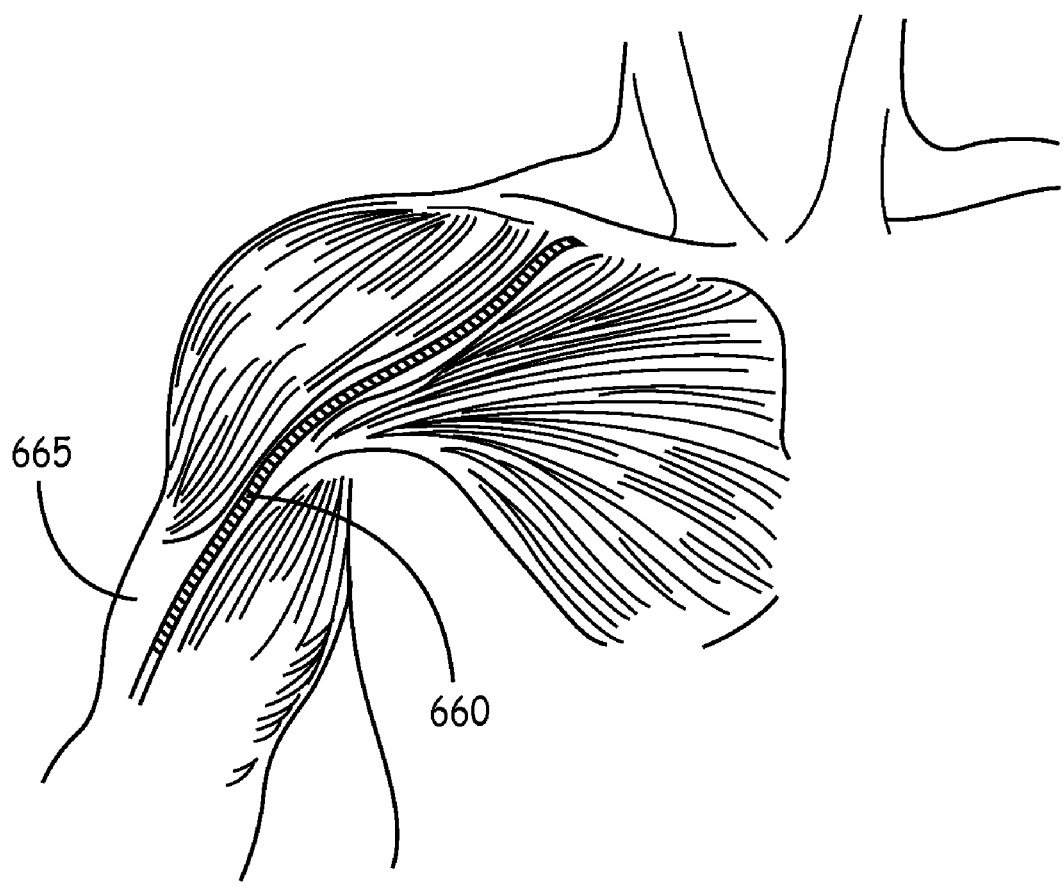
FIG. 19 illustrates the anatomical location of the cephalic vein.

As illustrated in FIG. 17, the initial entry point 600 may be positioned quite distant relative to the location of the housing 12. FIG. 19 illustrates the position of the cephalic vein 660 which flows into the subclavian vein 504 and is accessible along the arm 665 of the patient. Thus, the initial entry point 600 may be made in the cephalic vein 660 with the tether 70 then anchored to tissue in the arm 605.

After implantation, it may be necessary or desirable to access the IVMD 10. The proximal end 74 of the tether 70 is located and, e.g., the subclavian vein 504 is accessed. The housing 12 may be moved or removed/explanted via the tether 70 and any associated leads 60 can likewise be moved, explanted, tested or otherwise manipulated. In addition, components may be added or replaced on housing 12 without requiring removal. As identification of the proximal end 74 of the tether 70 facilitates such procedures, the proximal end 74 may include a radiopaque marker for identification with various imaging technologies, such as X-ray imaging or fluoroscopy. Of course, the entirety of the tether 70 may likewise be radiopaque. Alternatively, or in addition thereto, the proximal end 74 may be felt by applying pressure in the area. The configuration and anchoring of the proximal end 74 will determine whether this is possible and a balance is selected between patient perception of the proximal end, and the ability to locate the tether 70 manually, and the ease or pressure required to locate the tether 70 manually. As yet another alternative, the subclavian vein 504 (or any vein/artery with a tether 70) is accessed via a new puncture distal to the proximal end 74. The tether 70 is then located and manipulated. This may involve severing the tether 70 and if appropriate, reattaching or re-anchoring the tether 70.

As illustrated in FIG. 17, the IVMD 10 is secured at two locations; the first being where the proximal end 74 of the tether 70 is sutured and the second where the lead 60 is affixed to the atrial wall. In some embodiments, the nature of the lead 60 (or the absence thereof) may permit the distal end of that lead 60 or the housing 12 to move freely and remain unsecured. For example, lead 60 may include a pressure sensor or temperature sensor. While such sensors may still include an attachment mechanism, it is possible to permit them to remain unattached. In addition to having the tether 70 anchored and having one or more leads 60 anchored, the flow of blood is directed towards the heart; which generally assists with maintaining the position of housing 12 as this flow generates force against the anchored portion of the tether 70. This represents a relatively simple implantation procedure in that additional retention mechanisms are not required.

As indicated, the subclavian vein 504 and superior vena cava 506 are not the only potential implant locations. A variety of other locations will be able to utilize blood flow and gravity in combination with the tether 70 to secure IVMD 10. Of course, IVMD 10 may be implanted in other locations wherein this effect is not available or sufficient. In addition, there may be other reasons to further secure various portions of IVMD 10. In one embodiment, retractable members are provided that expand against a vessel wall to secure the IVMD 10. The retractable members are collapsed for subsequent movement or explantation. Such structures are illustrated in published PCT application WO 2004/110263 which is herein incorporated by reference.

Figure 20:
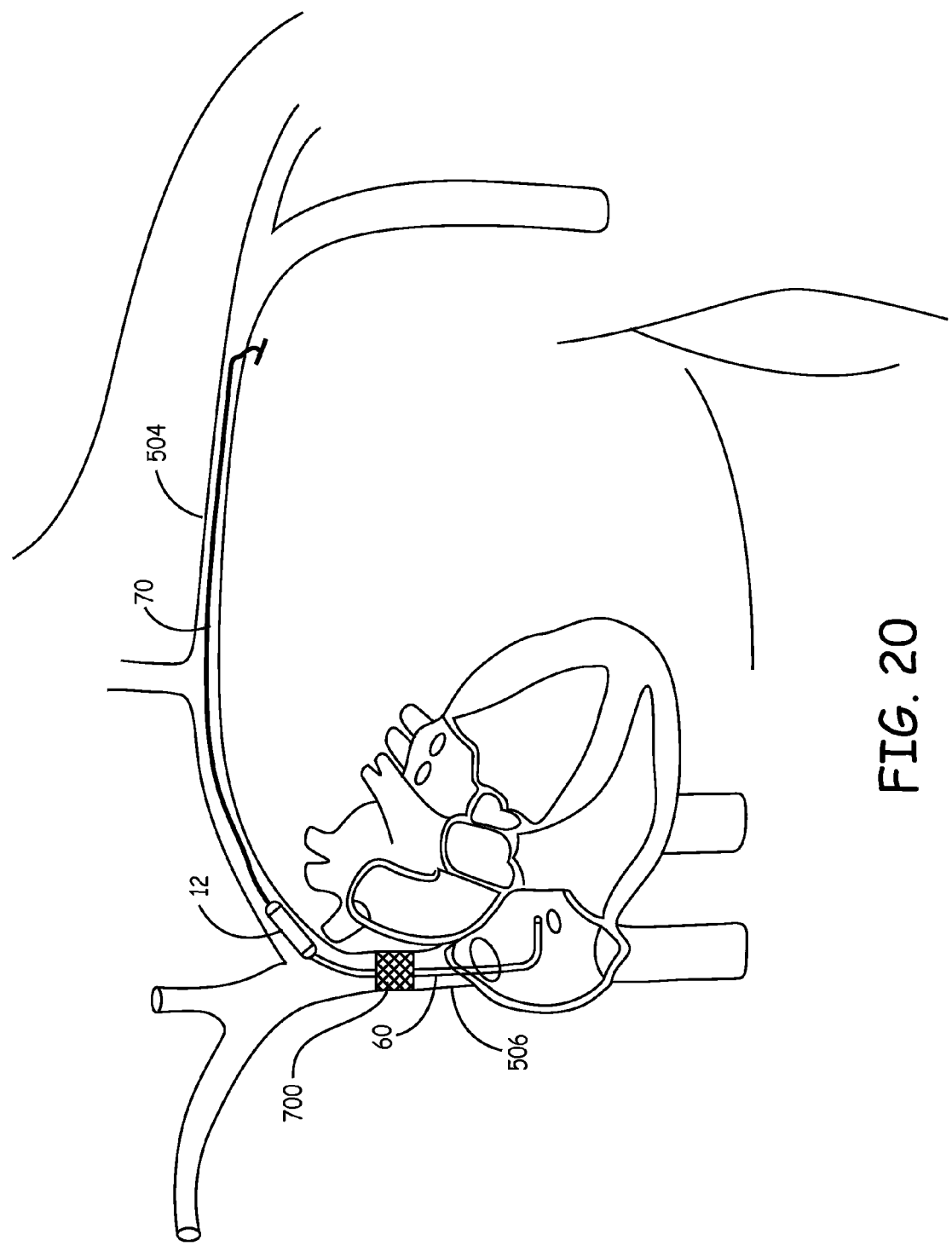
FIG. 20 illustrates an IVMD implanted in the superior vena cava having an auxiliary support member further anchoring the lead.

FIG. 20 illustrates an IVMD 10 implanted in substantially the same position as illustrated in FIG. 17. In this embodiment, an expansion member 700 is expanded within the superior vena cava 506. Expansion member 700 presses the lead 60 against an interior wall of the vessel, further securing the lead 60 in place. Expansion member 700 may be a self expanding member made from shape-memory material or from material having a spring force that is restrained by e.g., a catheter until deployed. Alternatively, expansion member 700 is mechanically expanded by a balloon catheter or similar deployment mechanism. The use of such a member is generally not required when both ends of the IVMD are secured and blood flow is not pulling against an implanted lead. Such an expansion member may be useful when the lead 60 is otherwise unsecured or IVMD 10 is positioned in a location where blood flow or other forces might negatively affect the implant. It should be appreciated that the expansion member 700 may be used for one or more leads, the housing 12, the tether 70 or any combination thereof.

Figure 21B:
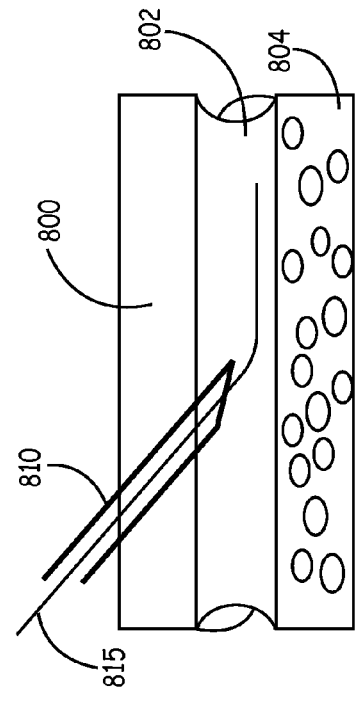
FIG. 21A-21J illustrate the insertion and anchoring of an IVMD.
Figure 21A:
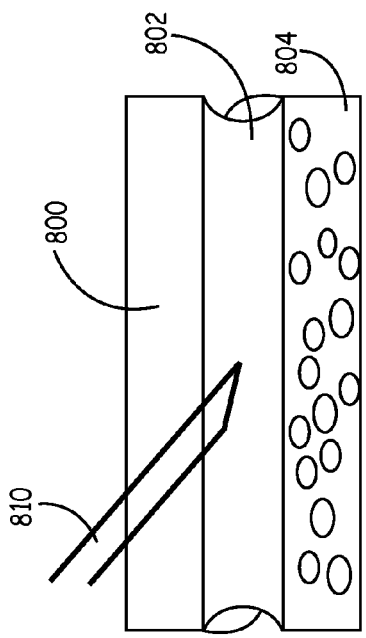
Figure 21D:
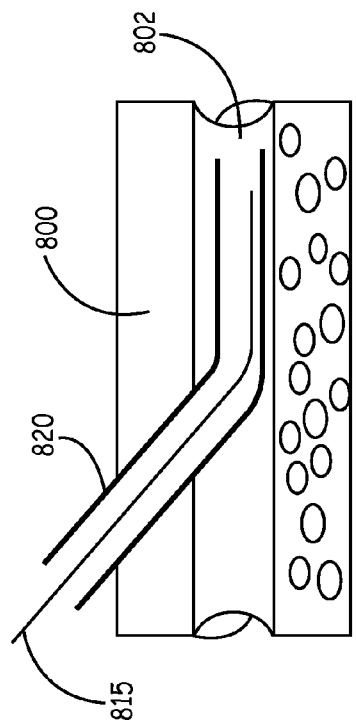

FIGS. 21A-21J schematically illustrate implantation of the IVMD 10. In FIG. 21A, a needle 810 is used to percutaneously pierce and enter a vessel 802, such as for example the subclavian vein or cephalic vein. The needle 810 passes through the skin 800; in some cases access to the vein 802 may require piercing muscle or other tissue. Care is taken with the percutaneously puncture so that the needle does not pass entirely through the vessel 802 and into the underlying tissue 804.

Figure 21C:
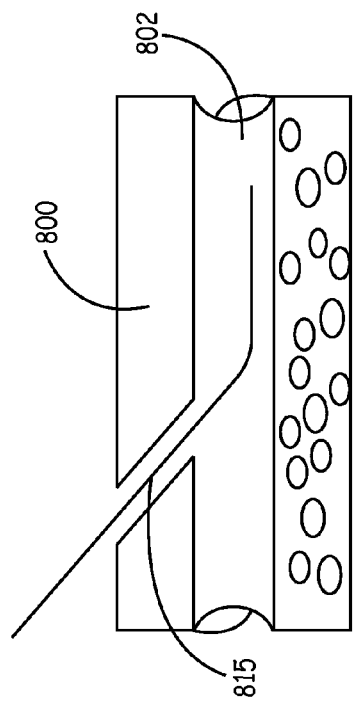
Figure 21E:
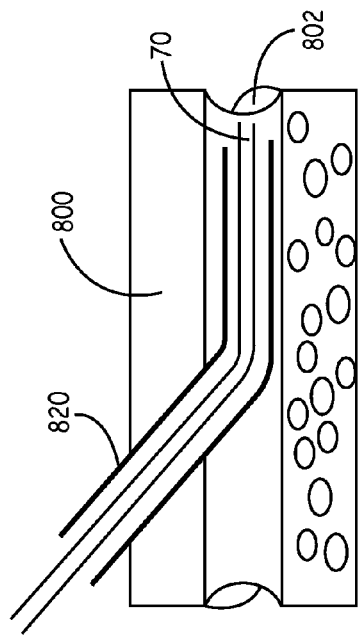

With the needle 810 positioned within the vessel 802, a guidewire 815 is passed through the needle 810 and into the vessel, as shown in FIG. 21B. While retaining the guidewire 815 in place, the needle 810 is withdrawn as illustrated in FIG. 21C. A deployment catheter 820 is inserted (FIG. 21D) into the vessel 802 over the guidewire 815. A dilation catheter may be used to expand the original puncture or the tissue may be cut if the opening is insufficient. Depending upon the configuration of the IVMD 10, the guidewire 815 and/or the deployment catheter 820 may be directed to the final implant location for a lead and/or for the housing of the IVMD 10. Alternatively, if a stylet or other external mechanism is utilized, the deployment catheter 820 need only provide access to the vessel 802 and the length of penetration is selected as desired.

Figure 21F:
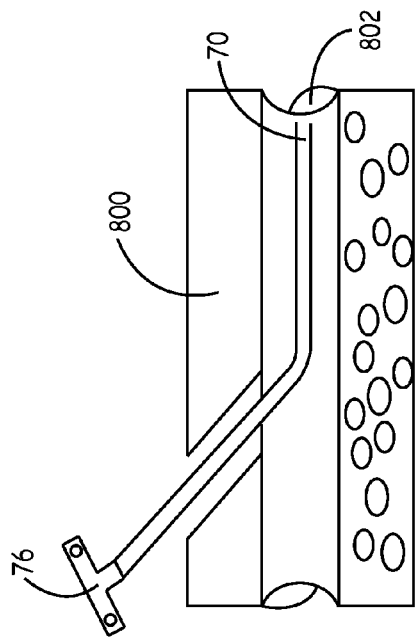
Figure 21G:
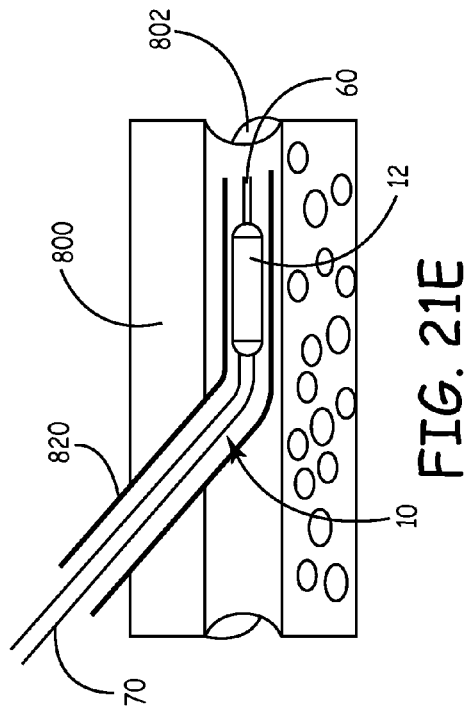

The IVMD 10 passes through the catheter 820 and enters the vessel 802. Again, multiple embodiments have been presented and the order of entry of certain components will vary accordingly. In this example, the lead 60 is directed first towards the implant site by e.g., a stylet directed through the lead or a stylet gripping an external portion of the lead; neither of which are illustrated in this figure. Trailing the lead 60 is the housing 12 followed by the tether 70. When the housing 12 and lead 60 are positioned, the tether 70 will include an excess amount exiting the incision site as illustrated in FIG. 21F. If additional intravascular securement mechanisms are utilized, they are deployed and configured. The tether 70 is cut (FIG. 21G) at sever point 830 with a sufficient amount of excess provided so that upon anchoring, enough slack remains to allow expected movement of the IVMD 10 within the vasculature. The cut tether now has a new proximal end 840.

Figure 21H:
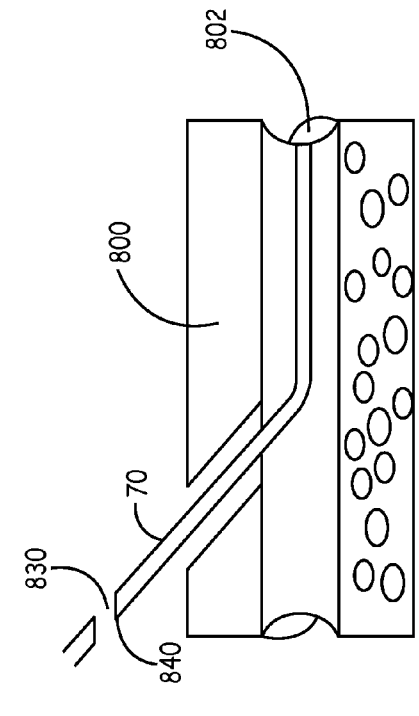
Figure 21I:
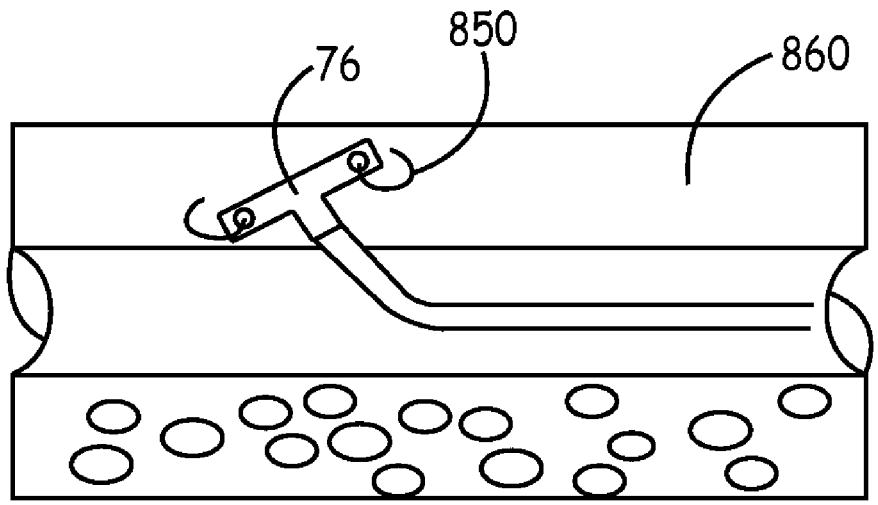
Figure 21J:
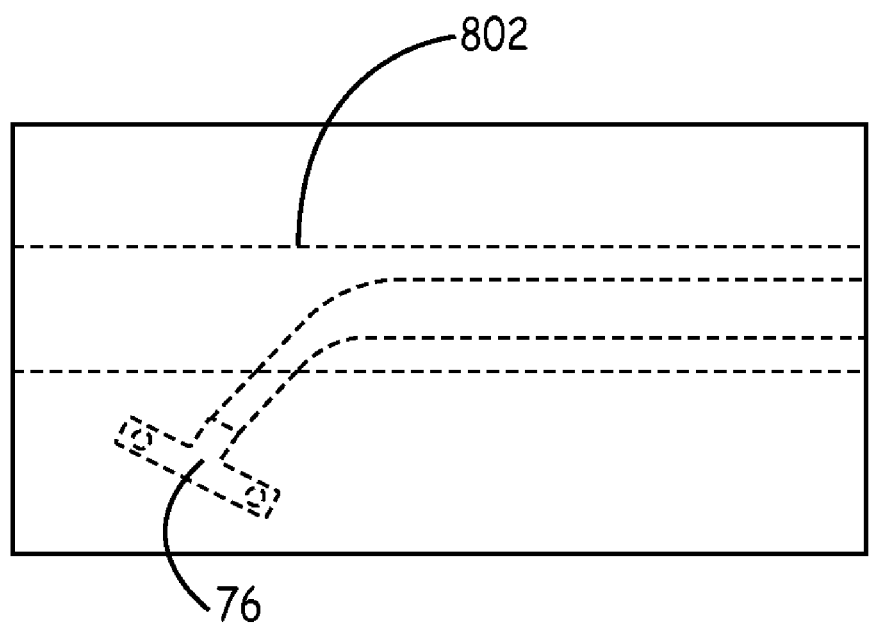

The new proximal end 840 is secured. As discussed, there are multiple methods to attach the tether 70. As illustrated, the T-anchor 76 is mechanically attached to the new proximal end 840 (FIG. 21H). The T-anchor 76 is then secured with sutures 850 to tissue proximate the incision site (FIG. 21I). The puncture or incision through the vessel 802 will heal around the tether 70 and if necessary, this process may be aided by additional suturing or other techniques. The T-anchor 76 will remain below the surface 860 of the skin 800, with the actual depth/distance from the surface 860 determined by the medical practitioner, the depth of the incision, and the site of implant. It should be appreciated that the anchor 76 may be affixed to skin tissue, muscle or even the vasculature wall. The final position of the anchor 76 may therefore be subcutaneous or submuscular. As illustrated in FIG. 21J, the anchor 76 may be secured some distance from the vessel 802. This may require an additional minor incision, but allows the anchor point to be selected disparate from the puncture through the vessel 802.

Figure 22A:
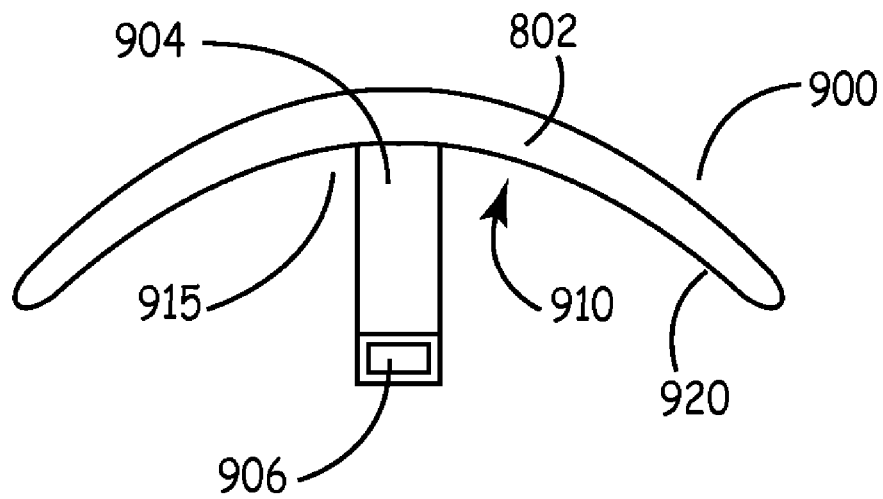
FIGS. 22A-22B illustrate a tether anchor.
Figure 22B:
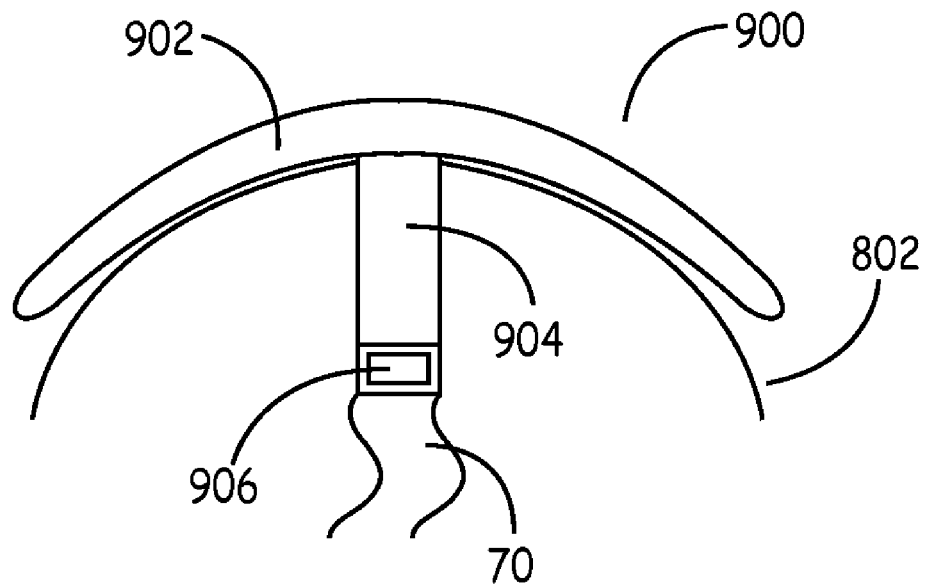

FIGS. 22A and 22B are side elevational sectional views that illustrate an external vasculature anchor 900 (EV anchor). As previously discussed, the T-anchor 76 is sutured or otherwise attached to tissue external to the vessel 802. The EV anchor 900 is configured for direct attachment to an external wall of the vessel 802. The EV anchor 900 has an arcuate attachment pad 902 with a tether connection rod 904 depending therefrom. A tether attachment opening 906 is provided at a distal end of the rod 904 so that the tether 70 is coupleable to the rod 904. The rod 904 penetrates the vessel 802 (though the drawings are not meant to be to scale) and serves as the anchor for the tether 70. The arcuate attachment pad 902 is large in comparison to the rod 904 so that the force generated against the vessel 802 is dispersed over a larger surface area.

The EV anchor 900 includes an interior concave surface 910 that is placed in contact with the vessel wall. This surface 910 is subdivided into a first region 915 proximate the rod 904 and the remainder of the surface 920. Various drug eluting or traditional coatings may be applied to the interior surface 910. For example, in the first region 915, where the rod 904 enters the vessel 802, adhesives, steroids, coagulants or other materials are provided to facilitate the closure and healing of the puncture. The second region 920 may be utilized for more adhesion or simply for mechanical support. The attachment pad 902 is meant to generally conform to the shape of the exterior wall of the vessel 802. To that end, the pad 902 may be flexible or malleable. Furthermore, while illustrated as extending about less than half the circumference of the vessels 802, it should be appreciated that the pad 902 may extend about a greater portion of the vessel 802 and may completely surround the vessel 802.

Figure 23:
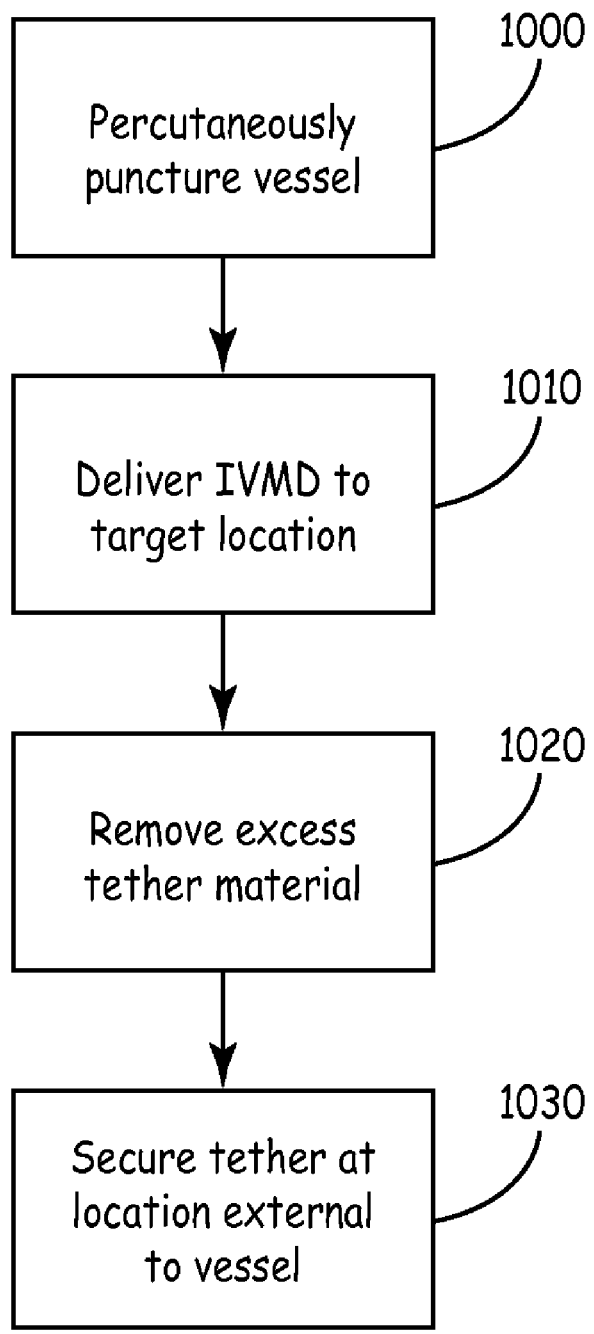
FIG. 23 is a flowchart describing a process for implanting an IVMD.

FIG. 23 is a flowchart with an overview of the steps for implanting the IVMD 10 consistent with the teachings of the present invention and as described in greater detail above. The appropriate point of entry (e.g., subclavian vein) is identified and a percutaneous puncture is made (1000). If necessary, this opening is enlarged and any necessary catheter, guidewire or stylet is utilized to insert, deliver and attach the housing, leads and any other intravascular components of the IVMD 10 (1010). The tether 70 extends from the now delivered housing 12 to the entry site and excess tether is cut and discarded (1020). Finally, the tether is secure external to the vessel so as to anchor the IVMD 10 (1030).

While various embodiments have been shown and described, the present invention is not meant to be limited by these embodiments. Furthermore, the embodiments may be combined in numerous ways without departing from the teachings of the present invention, even when not specifically illustrated. Variations and modifications may be made without departing from the spirit and scope of the present invention.

We claim:

1. A method comprising:
   implanting a lead at an anatomical location;
   implanting a housing having a power supply within a vascular structure, wherein the lead is operably coupled with the housing;
   securing the housing within the vascular structure via a tether comprising a distal end and a proximal end, wherein the proximal end is anchored outside the vascular structure and the distal end is coupled to the housing; and
   replacing the power supply subsequent to implanting the lead, implanting the housing and securing the housing, without removing the lead from the anatomical location.

2. The method of claim 1, wherein replacing the power supply further comprises:
   accessing the tether post-implant;

removing the housing with the power supply;
implanting a second housing with a second power supply by directing the second housing with the tether; and
coupling the second housing to the lead, wherein the lead remains attached to the anatomical location.

3. The method of claim 1, wherein replacing the power supply further comprises:
accessing the tether post-implant;
removing a portion of the housing including the power supply while leaving a tethered section of the housing;
implanting a second portion of the housing including a charged power supply by directing the second portion of the housing with the tether;
coupling the second portion of the housing with the charged power supply to the tethered section of the housing.

4. An intravascular medical device (IVMD) comprising:
a housing including one or more components of the IVMD;
means for securing the housing within a vascular structure with a tether having a proximal end coupleable to a location exterior to the vascular structure and a distal end coupleable to the housing, wherein the tether is configured to permit the housing module to move within the vascular structure in response to blood flow within the vascular structure;
means for powering the IVMD; and
means for modifying the means for powering.

5. The IVMD of claim 4, wherein the means for powering include a battery and the means for modifying include means for recharging the battery.

6. The IVMD of claim 4, wherein the means for modifying include means for replacing a first portion of the IVMD post implant without removing a second portion of the IVMD whereby the replaced first portion includes a charged battery.

7. An intravascular medical device (IVMD) comprising:
a housing module;
a lead coupleable with a first end of the housing module;
a tether comprising a proximal portion and a distal portion, the distal portion coupled to the housing module, wherein the tether is configured to secure the housing module at a position within a vascular structure when the proximal portion of the tether is anchored at an anchor point distant from the position of the housing module, and the tether is configured to permit the housing module to move within the vascular structure in response to blood flow within the vascular structure; and
a power source operably coupled with the housing module.

8. The IVMD of claim 7, wherein the power source includes a rechargeable battery contained within the housing module.

9. The IVMD of claim 7, further comprising:
a recharging module coupled with the battery to recharge the battery.

10. The IVMD of claim 9, wherein the recharging module further comprises a receiver to receive radio frequency (RF) energy and a converter to convert the RF energy into electrical energy to recharge the battery.

11. The IVMD of claim 9, wherein the recharging module further comprises a motion activated generator that converts motions into electrical current to recharge the battery.

12. The IVMD of claim 11, wherein the motion activated generator includes a magnet and a coil.

13. The IMVD of claim 11, wherein the motion activated generator includes means for converting fluid motion around the IVMD into electrical energy.

14. The IVMD of claim 9, wherein the recharging module includes means for collecting charge from tissue proximate the IMVD.

15. The IVMD of claim 7, wherein the power source further comprises means for providing power to the IVMD by converting non-electrical energy into electrical energy.

16. The IVMD of claim 15, wherein the non-electrical energy is motion.

17. The IVMD of claim 15, wherein the non-electrical energy is fluid flow.

18. The IVMD of claim 15, further comprising a battery wherein the means for providing power provides the power to the battery.

19. The IVMD of claim 7, wherein the power source is replaceable separate from the lead.

20. The IVMD of claim 7, wherein the tether is configured to be anchored at a single point.

21. The IVMD of claim 7, further comprising an anchor configured to anchor the proximal portion of the tether.

22. The IVMD of claim 7, wherein the housing module contains an implantable pulse generator configured to generate electrical stimulation energy.

23. An intravascular medical device (IVMD) comprising:
a housing module;
a lead coupleable with a first end of the housing module;
a tether comprising a proximal portion and a distal portion, the distal portion coupled to the housing module, wherein the tether is configured to secure the housing module at a position within a vascular structure when the proximal portion of the tether is anchored at an anchor point distant from the position of the housing module, and the tether is configured to counteract forces of blood flow against the housing module, thereby securing the housing module; and
a power source operably coupled with the housing module.

24. A method comprising:
implanting a housing module within a vascular structure, wherein a power supply is operably coupled with the housing module and a lead is coupled to the housing module; and
securing the housing module within the vascular structure via a tether, the tether comprising a proximal portion and a distal portion, wherein the distal portion is coupled to the housing module, wherein securing the housing within the vascular structure via the tether comprises securing the proximal portion of the tether at an anchor point distant from the housing module, and the tether is configured to permit the housing module to move within the vascular structure in response to blood flow within the vascular structure.

25. The method of claim 24, wherein the tether is anchored at a single point.

26. The method of claim 24, wherein the tether further comprises an anchor configured to anchor the tether at the anchor point.

27. The method of claim 24, wherein the housing module contains an implantable pulse generator configured to generate electrical stimulation energy.

28. A method comprising:
implanting a housing module within a vascular structure, wherein a power supply is operably coupled with the housing module and a lead is coupled to the housing module; and
securing the housing within the vascular structure via a tether, the tether comprising a proximal portion and a distal portion, wherein the distal portion is coupled to the housing module, wherein securing the housing within the vascular structure via the tether comprises securing the proximal portion of the tether at an anchor point distant from the housing module, and the tether is configured to counteract forces of blood flow against the housing module, thereby securing the housing module.

29. A method comprising:

implanting a housing module within a vascular structure, wherein a power supply is operably coupled with the housing module and a lead is coupled to the housing module; and securing the housing module within the vascular structure via a tether, the tether comprising a proximal portion and a distal portion, wherein the distal portion is coupled to the housing module, wherein securing the housing within the vascular structure via the tether comprises securing the proximal portion of the tether at an anchor point distant from the housing module, and the anchor point comprises an extravascular location.

* * * * *

UNITED STATES PATENT AND TRADEMARK OFFICE
CERTIFICATE OF CORRECTION

PATENT NO.      : 7,627,376 B2                                           Page 1 of 1
APPLICATION NO. : 11/342735
DATED           : December 1, 2009
INVENTOR(S)     : Dennis et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 767 days.

Signed and Sealed this

Second Day of November, 2010

David J. Kappos
*Director of the United States Patent and Trademark Office*